(12) United States Patent
Johnson et al.

(10) Patent No.: US 7,625,903 B2
(45) Date of Patent: Dec. 1, 2009

(54) ANTHRANILAMIDE INHIBITORS OF AURORA KINASE

(75) Inventors: Neil W. Johnson, Collegeville, PA (US); Deborah L. Bryan, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 12/019,730

(22) Filed: Jan. 25, 2008

(65) Prior Publication Data

US 2008/0182852 A1    Jul. 31, 2008

Related U.S. Application Data

(60) Provisional application No. 60/886,676, filed on Jan. 26, 2007.

(51) Int. Cl.
*A61K 31/497* (2006.01)
*C07D 403/00* (2006.01)

(52) U.S. Cl. .................. 514/252.14; 544/295

(58) Field of Classification Search .............. None
See application file for complete search history.

(56) References Cited

U.S. PATENT DOCUMENTS

2006/0009453 A1    1/2006    Geuns-Meyer et al.

FOREIGN PATENT DOCUMENTS

| EP | 1184376 | 2/2005 |
|---|---|---|
| EP | 1598343 | 11/2005 |
| WO | WO0164656 | 9/2001 |
| WO | WO03037877 | 5/2003 |
| WO | WO03078404 | 9/2003 |
| WO | WO2004074244 | 9/2004 |
| WO | WO2004080980 | 9/2004 |
| WO | WO2005016894 | 2/2005 |
| WO | WO2005026130 | 3/2005 |
| WO | WO2005026158 | 3/2005 |
| WO | WO2006021454 | 3/2006 |
| WO | WO2007089768 | 8/2007 |
| WO | WO2008073687 | 6/2008 |

OTHER PUBLICATIONS

Goldman et al [Editors] "Chapter 198: Principles of Cancer Therapy." Cecil's Textbook of Medicine (Twenty-First Edition, vol. 1). W.B. Saunders Company, 2000. pp. 1060-1074.*
Cancer, Merck Manual Home Edition, pp. 1-2, Retrieved on Mar. 11, 2009.*
Cheethem, et al, "Crystal Structure of Aurora-2, an Oncogenic serine/Threonine Kinase." *Journal of Biological Chemistry*., Nov. 8, 2002: 277:42419-42422: pp. 44420-44421, Fig 1 and 2.

* cited by examiner

*Primary Examiner*—Patricia A. Duffy
*Assistant Examiner*—Anna Pagonakis
(74) *Attorney, Agent, or Firm*—Reid S. Willis; John Lemanowicz

(57) ABSTRACT

The present invention relates to a compound represented by the following formula:

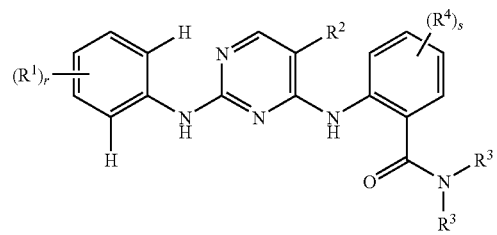

or a pharmaceutically acceptable salt thereof;
where $R^1$, $R^2$, $R^3$, $R^4$, r and s are as previously defined.
Compounds of the present invention are useful in the treatment of diseases associated with Aurora kinase activity such as cancer.

4 Claims, No Drawings

ANTHRANILAMIDE INHIBITORS OF AURORA KINASE

This application claims benefit under 35 U.S.C. 119 to Provisional Application No. 60/886,676 filed Jan. 26, 2007.

BACKGROUND OF THE INVENTION

The present invention relates to anthranilamide compounds, compositions, and medicaments thereof, as well as methods of treatments therefore. These anthranilamide compounds are useful in the treatment of diseases associated with Aurora kinase activity.

Protein kinases catalyze the phosphorylation of hydroxylic amino acid side chains in proteins by the transfer of the γ-phosphate of ATP-$Mg^{2+}$ to form a mono-phosphate ester of serine, threonine or tyrosine. Studies have shown that protein kinases are key regulators of many cell functions, including signal transduction, transcriptional regulation, cell motility and cell division. Several oncogenes have also been shown to encode protein kinases, suggesting that kinases may play a role in oncogenesis.

The protein kinase family of enzymes is typically classified into two main subfamilies: protein tyrosine kinases and protein serine/threonine kinases, based on the amino acid residue they phosphorylate. Aberrant protein serine/threonine kinase activity has been implicated or is suspected in a number of pathologies such as rheumatoid arthritis, psoriasis, septic shock, bone loss, cancers and other proliferative diseases. Tyrosine kinases play an equally important role in cell regulation. These kinases include several receptors for molecules such as growth factors and hormones, including epidermal growth factor receptor, insulin receptor and platelet derived growth factor receptor. Studies have indicated that many tyrosine kinases are transmembrane proteins with their receptor domains located on the outside of the cell and their kinase domains on the inside. Accordingly, both kinase subfamilies and their signal transduction pathways are important targets for drug design.

Since its discovery in 1997, the mammalian Aurora family of serine/threonine kinases has been closely linked to tumorigenesis. The three known mammalian family members, Aurora-A ("2"), B ("1") and C ("3"), are highly homologous proteins responsible for chromosome segregation, mitotic spindle function and cytokinesis. Aurora expression is low or undetectable in resting cells, with expression and activity peaking during the G2 and mitotic phases in cycling cells. In mammalian cells proposed substrates for the Aurora A and B kinases include histone H3, CENP-A, myosin II regulatory light chain, protein phosphatase 1, TPX2, INCENP, p53 and survivin, many of which are required for cell division.

The Aurora kinases have been reported to be over-expressed in a wide range of human tumors. Elevated expression of Aurora-A has been detected in colorectal, ovarian and pancreatic cancers and in invasive duct adenocarcinomas of the breast. High levels of Aurora-A have also been reported in renal, cervical, neuroblastoma, melanoma, lymphoma, pancreatic and prostate tumor cell lines. Amplification/over-expression of Aurora-A is observed in human bladder cancers and amplification of Aurora-A is associated with aneuploidy and aggressive clinical behavior. Moreover, amplification of the Aurora-A locus (20q13) correlates with poor prognosis for patients with node-negative breast cancer. In addition, an allelic variant, isoleucine at amino acid position 31, is reported to be a low-penetrance tumor-susceptibility gene and displays greater transforming potential than the phenylalanine-31 variant and is associated with increased risk for advanced and metastatic disease. Like Aurora A, Aurora-B is also highly expressed in multiple human tumor cell lines, including leukemic cells. Levels of Aurora-B increase as a function of Duke's stage in primary colorectal cancers. Aurora-C, which is normally only found in germ cells, is also over-expressed in a high percentage of primary colorectal cancers and in a variety of tumor cell lines including cervical adenocarinoma and breast carcinoma cells.

The literature supports the hypothesis that in vitro an inhibitor of Aurora kinase activity would disrupt mitosis causing cell cycle defects and eventual cell death. Therefore, in vivo, an Aurora kinase inhibitor should slow tumor growth and induce regression. For example, Hauf et al. describe an Aurora B inhibitor, Hesperadin, that causes defects in chromosomal segregation and a block in cytokinesis, thereby resulting in polyploidy [Hauf, S et al. JCB 161(2), 281-294 (2003)]. Ditchfield et al. have described an equipotent inhibitor of Aurora A and B (ZM447439) that causes defects in chromosome alignment, chromosome segregation and cytokinesis [Ditchfield, C. et al., JCB 161(2), 267-280 (2003)]. Furthermore, the authors show that proliferating cells, but not cell-cycle arrested cells, are sensitive to the inhibitor. Efficacy of a potent Aurora A and B inhibitor in mouse and rat xenograft models was recently reported [Harrington, E. A. et al., Nature Medicine 10(3), 262-267, (2004)]. These results demonstrate that inhibition of Aurora kinases can provide a therapeutic window for the treatment of proliferative disorders such as cancer (see Nature, Cancer Reviews, Vol. 4, p 927-936, December 2004, for a review by N. Keen and S Taylor, which outlines the therapeutic potential of Aurora kinase inhibitors for the treatment of cancer).

In view of the teachings of the art, there is a need for the discovery of kinase activity inhibitors, in particular, compounds that inhibit the activity of Aurora kinases.

SUMMARY OF THE INVENTION

In a first aspect, the present invention relates to a compound represented by the following Formula I:

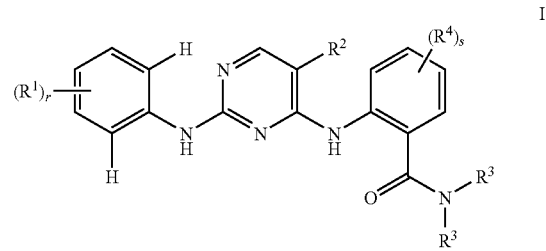

or a pharmaceutically acceptable salt thereof;

wherein each $R^1$ is independently H, —$(CH_2)_n N(R^5)_2$, —O—$(CH_2)_p N(R^5)_2$, $C(O)N(R^5)_2$, —$(CH_2)_n SO_2(NH)_q R^6$, COOH, $C_1$-$C_6$-alkyl, $C_1$-$C_6$-alkoxy, $CF_3$, halo, or CN;

with the proviso that at least one $R^1$ is —$(CH_2)_n$—$N(R^5)_2$, —O—$(CH_2)_p N(R^5)_2$, $C(O)N(R^5)_2$, —$(CH_2)_n SO_2(NH)_q R^6$, or COOH;

n is 0, 1, 2, or 3; p is 2 or 3; q is 0 or 1; r is 1, 2, or 3; s is 0, 1 or 2;

$R^2$ is H, halo; $C_1$-$C_3$-alkyl, $C_1$-$C_3$-alkoxy, CN, nitro, or $CF_3$;

each $R^3$ is independently H, heterocycloalkyl, cycloalkyl, phenyl, morpholino-$CH_2CH_2$-phenyl or $C_1$-$C_6$-alkyl optionally substituted with hydroxy, amino, $C_1$-$C_6$-alkylamino, di-$C_1$-$C_6$-alkylamino, trifluoromethyl, tetrahydrofuranyl, pyridinyl, or imidazolyl; or, each $R^3$, together with the nitrogen to which they are attached, form a 5- or 6-membered cyclic group optionally substituted with hydroxy, $C_1$-$C_6$-alkyl, hydroxy-$C_1$-$C_3$-alkyl, morpholino, —C(O)CH$_3$, di-$C_1$-$C_2$-alkylamino, or —C(O)NH$_2$.

$R^4$ is halo, $C_1$-$C_3$-alkyl, or $C_1$-$C_3$-alkoxy;

each $R^5$ is independently $C_1$-$C_6$-alkyl, or —C(O)CH$_3$ or, together with the nitrogen to which they are attached, form a 5- or 6-membered cyclic group optionally substituted with hydroxy, $C_1$-$C_6$-alkyl, hydroxy-$C_1$-$C_3$-alkyl, morpholino, —C(O)CH$_3$, di-$C_1$-$C_2$-alkylamino, or —C(O)NH$_2$; and $R^6$ is $C_1$-$C_6$-alkyl, $(R^7)_x$-phenyl-(C(O))$_y$—, or $(R^8)_z$-heteroaryl-(C(O))$_y$—, where x is 0, 1, 2, or 3; z is 0, 1, or 2; y is 0 or 1;

$R^7$ is halo, $C_1$-$C_3$-alkyl or $C_1$-$C_3$-alkoxy; and $R^8$ is halo, $C_1$-$C_3$-alkyl or $C_1$-$C_3$-alkoxy.

The present invention also relates to a composition comprising a) the compound of formula 1 or a pharmaceutically acceptable salt thereof; and b) at least one pharmaceutically acceptable excipient.

In a further aspect, the present invention also relates to a method for treating cancer comprising administering to a patient in need thereof the compound of formula 1, or a pharmaceutically acceptable salt thereof.

The present invention also relates to a method for treating cancer comprising administering to a patient in need thereof an effective amount of a composition comprising a) the compound of formula 1 or a pharmaceutically acceptable salt thereof, and b) at least one pharmaceutically acceptable excipient.

DETAILED DESCRIPTION OF THE INVENTION

In one aspect, the present invention relates to a compound represented by the following formula:

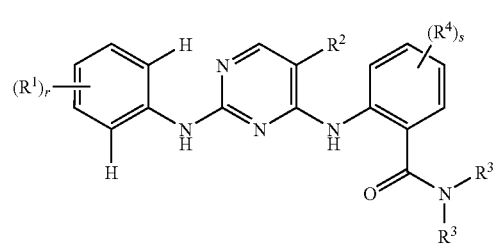

(I)

where $R^1$, $R^2$, $R^3$, $R^4$, r and s are as previously defined.

As used herein, halo refers to fluoro, chloro, or bromo. $C_1$-$C_6$-alkyl refers to a linear or branched alkyl group including methyl, ethyl, n-propyl, isopropyl, n-butyl, isobutyl, t-butyl, n-pentyl, and n-hexyl.

Examples of suitable $C_1$-$C_6$-alkylamino groups include methylamino, ethylamino, n-propylamino, and isopropylamino; similarly, examples of $C_1$-$C_6$-dialkylamino groups include dimethylamino, diethylamino, methylethylamino, di-n-propylamino, and diisopropylamino. For the fragments —(CH$_2$)$_2$—N(R$^5$)$_2$, C(O)N(R$^5$)$_2$, and —O—(CH$_2$)$_p$N(R$^5$)$_2$, each $R^5$, together with the nitrogen to which they are attached, form a 5- or 6-membered cyclic group, optionally substituted with hydroxy, $C_1$-$C_6$-alkyl, hydroxy-$C_1$-$C_3$-alkyl, morpholino, —C(O)CH$_3$, di-$C_1$-$C_2$-alkylamino, or —C(O)NH$_2$.

Suitable examples of nitrogen-containing 5- and 6-membered cyclic groups include, but are not limited to, pyrrolidinyl, pyrrolidinonyl, piperidinyl, piperazinyl, oxopiperazinyl, and morpholino groups.

$C_1$-$C_3$-alkoxy refers to methoxy, ethoxy, n-propoxy, and n-isopropoxy.

As used herein, heterocycloalkyl refers to a 5- or 6-membered cyclic group that includes either an O, N, or S heteroatom or a combination thereof. Suitable heterocycloalkyl groups 1,3-dioxolanyl, tetrahydrofuranyl, pyrrolidinyl, pyrrolidinonyl, piperidinyl, piperazinyl, oxopiperazinyl, and morpholino groups.

Cycloalkyl is used herein to refer to cyclopropyl, cyclobutyl, cyclopentyl, or cyclohexyl groups.

In a further aspect, the compound is represented by the following Formula Ia:

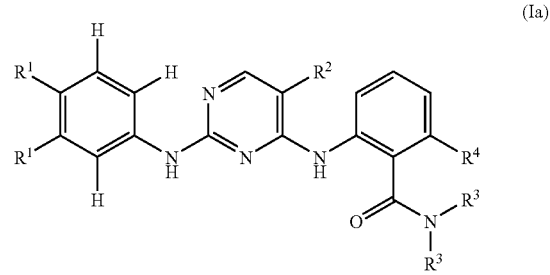

(Ia)

wherein $R^2$ is Cl, F, or CH$_3$; and $R^4$ is F or H.

In a further aspect, the compound is represented by Formula Ia wherein one $R^1$ is —(CH$_2$)$_n$—N(R$^6$)$_2$, and the other $R^1$ is H, methyl or methoxy.

In a further aspect, $R^2$ is CH$_3$ or F; each $R^3$ is independently H, CH$_3$, isopropyl, or hydroxyethyl; and each $R^5$ together with the nitrogen atom to which they are attached form a pyrrolidinyl, pyrrolidinonyl, piperidinyl, piperazinyl, oxopiperazinyl, methylpiperazinyl, or morpholino ring.

In a further aspect, n is 0; $R^2$ is CH$_3$; and each $R^3$ is independently CH$_3$ or isopropyl.

In a further aspect, the present invention is a compound of Formula I, or a pharmaceutically acceptable salt thereof, which compound is selected from the group consisting of:

2-{[5-fluoro-2-({3-[2-(4-morpholinyl)ethyl]phenyl}amino)-4-pyrimidinyl]amino}-N-(2-hydroxyethyl)benzamide;

(3R)-1-({2-[(5-fluoro-2-{[3-(4-methyl-1-piperazinyl)phenyl]amino}-4-pyrimidinyl)amino]phenyl}carbonyl)-3-pyrrolidinol;

(3R)-1-[(2-{[5-methyl-2-({3-[2-(4-morpholinyl)ethyl]phenyl}amino)-4-pyrimidinyl]amino}phenyl)carbonyl]-3-pyrrolidinol;

2-[(2-{[4-({[2-(ethylamino)ethyl]sulfonyl}methyl)phenyl]amino}-5-fluoro-4-pyrimidinyl)amino]-N-(1-methylethyl)benzamide;

2-[(5-fluoro-2-{[4-(4-piperidinyl)phenyl]amino}-4-pyrimidinyl)amino]-N-(1-methylethyl)benzamide;

2-[(5-fluoro-2-{[4-({[2-(methylsulfonyl)ethyl]amino}methyl)phenyl]amino}-4-pyrimidinyl)amino]-N-(1-methylethyl)benzamide; and N-(1-methylethyl)-2-[(5-methyl-2-{[3-(4-methyl-2-oxo-1-piperazinyl)phenyl]amino}-4-pyrimidinyl)amino]benzamide.

As used herein, pharmaceutically acceptable refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio. The skilled artisan will appreciate that pharmaceutically acceptable salts of compounds according to Formula (I) may be prepared. These pharmaceutically acceptable salts may be prepared in situ during the final isolation and purification of the compound, or by separately reacting the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminum, and zinc; and b) primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, malic acid, malonic acid, tartaric acid, citric acid, salicylic acid, benzoic acid, tannic acid, formic acid, stearic acid, lactic acid, ascorbic acid, p-toluenesulfonic acid, oleic acid, and lauric acid.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

Schemes

Compounds of formula (I) may be conveniently prepared by the methods outlined in Scheme 1 below. Compounds of formula (II) and (III) are commercially available or may be synthesized using techniques conventional in the art. The compounds of formula (II) and (III) may be reacted under reflux or microwave conditions to afford intermediate (IV).

The addition reaction is typically done using a polar, protic solvent such as n-butanol or iso-propanol. When compound (II) includes a functional group in need of protection, for example, a hydroxyl or amino group, an appropriate protecting group is advantageously used. Compounds of formula (IV) may then be reacted with an aniline (V), which is commercially available or may be synthesized using techniques conventional in the art, to afford a compound of formula (VI). The reaction is typically carried out in the presence of an acid such as, but not limited to, hydrochloric or trifluoroacetic in a suitable solvent such as, but not limited to, iso-propanol, n-butanol, 1,4-dioxane, ethanol or N,N-dimethylformamide at refluxing temperature or in a microwave apparatus at elevated temperature (from about 100 to about 180° C.).

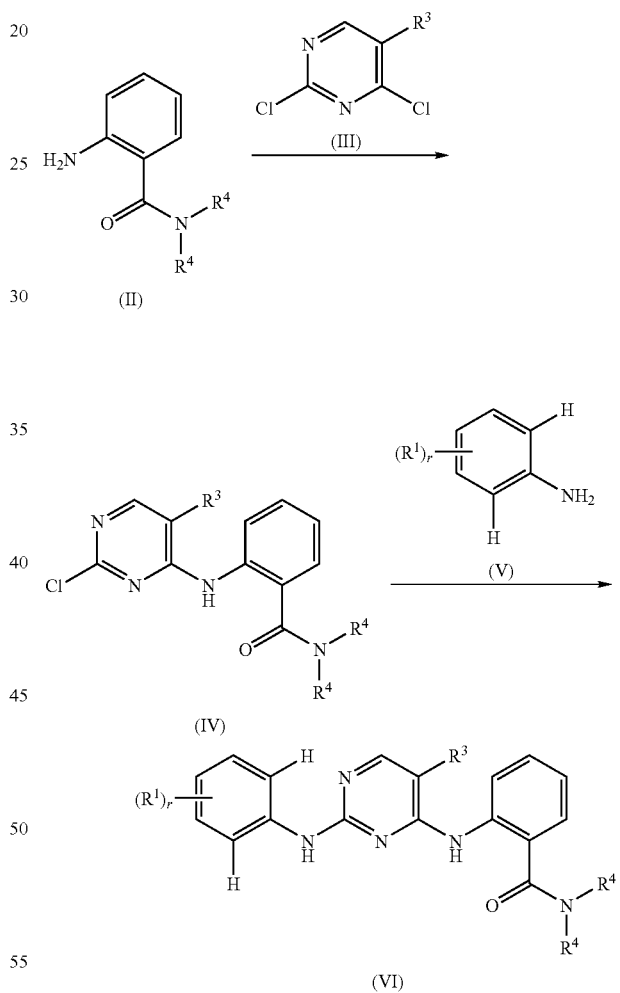

Scheme 1

Compound (II) may contain additional substituents. For example, as shown in Scheme 2, benzoxazine (VII), which is either commercially available or synthesized using techniques conventional in the art, can be ring-opened with an amine to form benzamide (VIII). This benzamide can then undergo addition with compound (III) to yield the compound of formula (IX).

Scheme 2

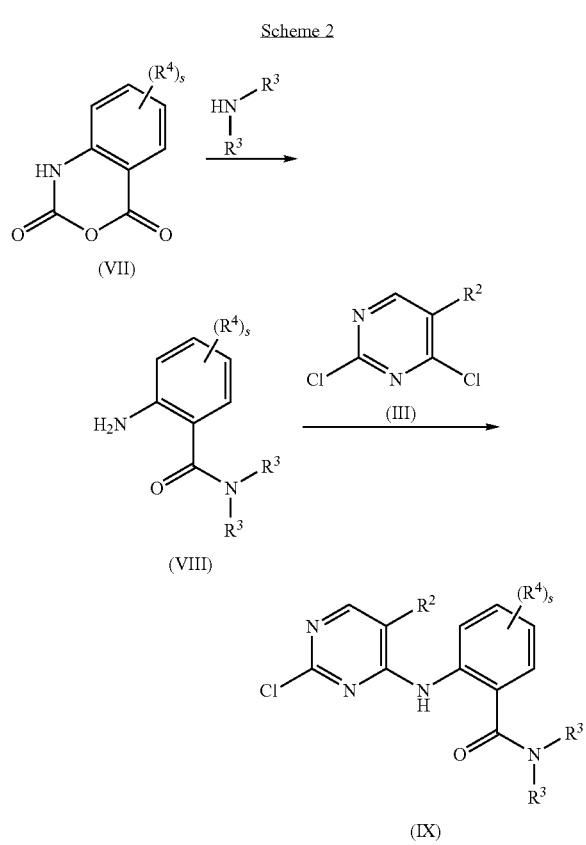

An alternative method for modifying the amide is shown in Scheme 3. Reaction of aminobenzoate (X) with pyrimidine (III) provides intermediate (XI). Aniline (V) can then be added to provide intermediate (XII). This pathway allows for the incorporation of amide amines in the final step to give products (VI).

Scheme 3

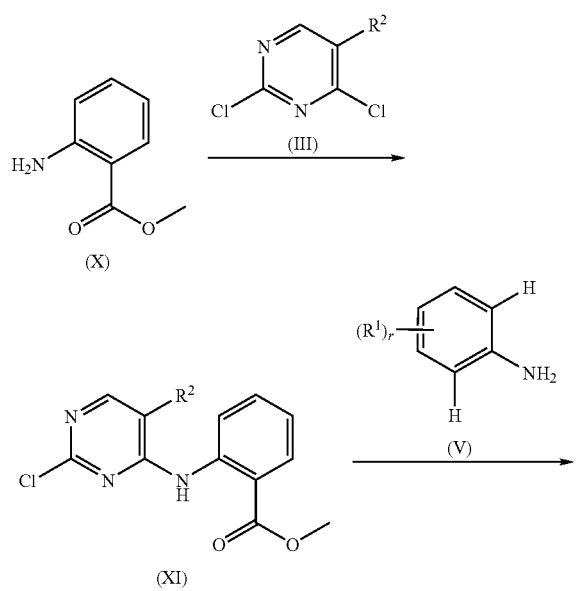

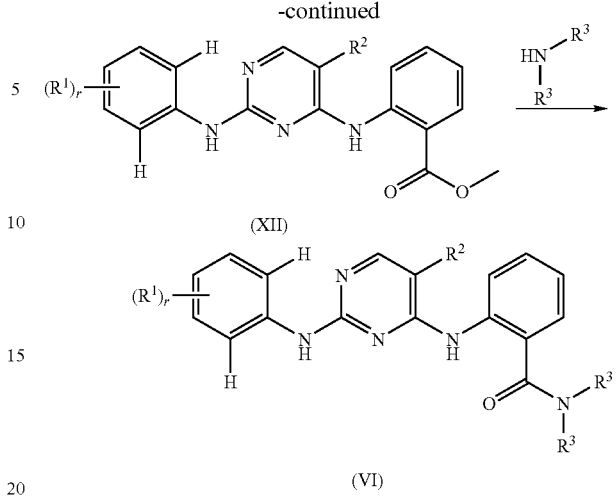

Biological Assays

Aurora A/TPX2 IMAP® Enzyme Activity Assay

Compounds of the present invention were tested for Aurora A/TPX2 protein kinase inhibitory activity in a substrate phosphorylation assay. This assay examines the ability of small molecule organic compounds to inhibit the serine phosphorylation of a peptide substrate, and was run in the IMAP® technology (Molecular Devices, Sunnyvale, Calif.) fluorescent polarization assay format. The method measures the ability of the isolated enzyme to catalyze the transfer of the gamma-phosphate from ATP onto the serine residue of a fluorescein-labeled synthetic peptide (5FAM-GRTGRRNSI-NH$_2$) (SEQ I.D. NO. 1). In a microwell assay format, the fluorescein-labeled peptide is phosphorylated in a kinase reaction. Addition of the IMAP® Binding System stops the kinase reaction and specifically binds the phosphorylated substrates. Phosphorylation and subsequent binding of the substrate to the beads (binding reagent) is detected by fluorescent polarization.

The substrate phosphorylation assays use recombinant human full-length Aurora A kinase expressed in baculovirus/Sf9 system. An N-terminal His-Thr-affinity tag was fused to the amino terminus of amino acids 2 through 403 of Aurora A. 5 nM okadaic acid was added during the last 4 h of expression (experimentally determined to enhance Aurora A's enzymatic activity). The enzyme was purified to approximately 70% purity by metal-chelate affinity chromatography.

Assays were performed in 384-well low volume black polystyrene plates (Greiner Bio-One, Longwood, Fla.). 5 µL of a 4 nM Aurora A enzyme was added to the wells containing 0.1 µl of test compound in 100% DMSO and incubated for 30 min followed by the addition of 5 µL reaction mixture resulting in a final assay volume of 10 µL containing 1 mM magnesium chloride, 2 µM ATP, 1 µM peptide substrate, 40 nM microtubule associated protein TPX2 peptide (1-43), 1.5 mM DTT, 25 mM NaCl, 0.15 mg/ML BSA and 0.01% Tween-20 in 50 mM HEPES, pH 7.2. The reaction was allowed to proceed for 120 min at room temperature and was terminated by the addition of 10 µL of a 1:500 dilution of Progressive Binding Reagent (nanoparticle beads) in the Molecular Devices proprietary 90% buffer A and 10% buffer B. After a 120 min incubation time the plates were read in a Analyst GT (Molecular Devices) in fluorescence polarization mode with excitation at 485 nM, emission at 530 nM and using the 505 nM dichroic lens.

Data is captured in parallel and perpendicular directions and converted to mp by the instrument. For dose response curves, data were normalized and expressed as percent inhibition using the formula 100*(1−(U−C2)/(C1−C2)) where U is the unknown value, C1 is the average of the high signal (0% inhibition) and C2 is the average of the low signal (100% inhibition) control wells. Curve fitting was performed with the following equation: $y=A+((B-A)/(1+(10^x/10^C)^D))$, where A is the minimum response, B is the maximum response, C is the log 10(XC50), and D is the slope. The results for each compound were recorded as pIC50 values (−C in the above equation).

Aurora B/INCENP IMAP® Enzyme Activity Assay

Compounds of the present invention were also tested for Aurora B/INCENP protein kinase inhibitory activity in a substrate phosphorylation assay. The substrate phosphorylation assay use recombinant human full-length Aurora B kinase expressed in baculovirus/Sf9 system. Following expression the culture is incubated with 50 nM okadaic acid for 1 h prior to purification. An N-terminal His-affinity tag was fused to the amino terminus of amino acids 1 through 344 of Aurora B. The expressed protein was purified by metal-chelate affinity chromatography. 5 µM Aurora B was activated in 50 mM Tris-HCl pH 7.5, 0.1 mM EGTA, 0.1% 2-mercaptoethanol, 0.1 mM sodium vanadate, 10 mM magnesium acetate, 0.1 mM ATP with 0.1 mg/mL GST-INCENP [826-919] at 30° C. for 30 min. Following activation the enzyme is then dialyzed into enzyme storage buffer and stored at −70° C.

Assays were performed in 384-well low volume black polystyrene plates (Greiner Bio-One, Longwood, Fla.). 5 µL of a 4 nM Aurora B/INCENP was added to the wells containing 0.1 µl of test compound in 100% DMSO and incubated for 30 min followed by the addition of 5 µL of a reaction mixture resulting in a final assay volume of 10 µL containing 2 mM magnesium chloride, 2.5 µM ATP, 1.25 µM peptide substrate (5FAM-GRTGRRNSI-$NH_2$), (SEQ I.D. NO. 1) 2 mM DTT, 25 mM NaCl, 0.15 mg/mL BSA, 0.01% Tween-20 in 50 mM HEPES, pH 7.5. The reaction was allowed to proceed for 120 min at room temperature and was terminated by the addition of 10 µL of a 1:500 dilution of Progressive Binding Reagent (nanoparticle beads) in the Molecular Devices proprietary 95% buffer A and 5% buffer B. After a 120-min incubation time the plates were read in a Analyst GT in fluorescence polarization mode with excitation at 485 nM, emission at 530 nM and using the 505 nM dichroic lens.

Data was captured as described for the Aurora A assay.

EXPERIMENTAL

The following examples are for illustrative purposes only and are not intended to limit the scope of the present invention. The compounds were named using ACD Name software (Advanced Chemistry Development). The dotted lines in the examples represent the point of attachment. All compounds have $pIC_{50}$ of greater than 6.0 for Aurora A and B.

A PE Sciex API 150 single quadrupole mass spectrometer (PE Sciex, Thornhill, Ontario, Canada) was used in tandem with a CTC PAL autosampler (LEAP Technologies, Carrboro, N.C.) The HPLC pump was a Shimadzu LC-10ADvp (Shimadzu Scientific Instruments, Columbia, Md.) operated at 0.3 mL/min and a linear gradient 4.5% solvent A to 90% solvent B in 3.2 min with a 0.4 min. hold. The mobile phase was composed of 100% ($H_2O$ 0.02% TFA) in vessel A and 100% ($CH_3CN$ 0.018% TFA) in vessel B. The stationary phase was Aquasil (C18) and the column dimensions were 1 mm×40 mm. Detection was done by UV at 214 nm, evaporative light-scattering (ELSD), and MS. Alternatively, an Agilent 1100 analytical HPLC system with LC/MS was used and operated at 1 mL/min and a linear gradient 5% solvent A to 100% solvent B in 2.2 min with a 0.4 min hold. The mobile phase was composed of 100% ($H_2O$ 0.02% TFA) in vessel A and 100% ($CH_3CN$ 0.018% TFA) in vessel B. The stationary phase is Zobax (C8) with a 3.5 µm partical size and the column dimensions were 2.1 mm×50 mm. Detection was also by UV at 214 nm, evaporative light-scattering (ELSD), and MS.

$^1$H-NMR (hereinafter "NMR") spectra were recorded at 400 MHz using a Bruker AVANCE 400 MHz instrument, with ACD Spect manager version 10 use for reprocessing. Multiplicities indicated are: s=singlet, d=doublet, t=triplet, q=quartet, m=multiplet, dd=doublet of doublets, dt=doublet of triplets etc. and br indicates a broad signal.

For preparative HPLC, solutions containing products were injected onto a Gilson preparative chromatography system with a 75×30 mm YMC CombiPrep ODS-A column (5 µm) at 50 mL/min with a 10 min gradient (5% $CH_3CN$ (0.1% formic acid) to 95% $CH_3CN$ (0.1% formic acid) in $H_2O$ (0.1% formic acid) and a 2 min hold); alternatively an Agilent 1100 Preparative Chromatography system was used (100×30 mm Gemini C18 column (5 µm) at 60 mL/min with a 10 min gradient from 5% $CH_3CN$ (0.1% formic acid) to 95% $CH_3CN$ (0.1% formic acid) in $H_2O$ (0.1% formic acid) and a 2 min hold).

Preparative normal phase chromatography was run using Analogix IntelliFlash280 system using SuperFlash Sepra Si 50 columns.

INTERMEDIATE 1

2-[(2,5-Dichloro-4-pyrimidinyl)amino]benzamide

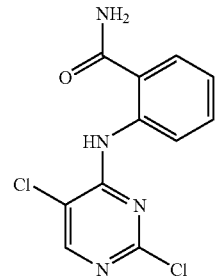

A round-bottomed flask was charged with 2,4,5-trichloropyrimidine (7 g, 38 mmol), ortho-anthranilamide (6.2 g, 45.8 mmol), diisopropyl-ethylamine (8 mL, 45.8 mmol) and 100 mL isopropanol. The flask was fitted with a reflux condenserand the reaction was heated to reflux and stirred for 18 h. A white solid appeared in the reaction mixture. The reaction was cooled to room temperature, ⅓ of the volume was removed under vacuum and the solid was filtered off and washed with isopropanol. After drying, the white solid (9 g, 32 mmol, 83% yield) was identified as 2-[(2,5-dichloro-4-pyrimidinyl)amino]benzamide. MS: M($C_{11}H_8Cl_2N_4O$)= 283.12, $(M+H)^+$=284 and 286.

EXAMPLE 1

2-[(5-Chloro-2-{[3-(1-pyrrolidinylmethyl)phenyl]amino}-4-pyrimidinyl)amino]benzamide

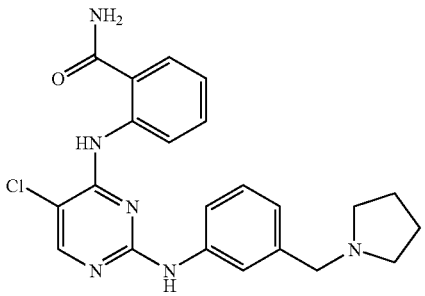

2-[(2,5-Dichloro-4-pyrimidinyl)amino]benzamide (200 mg, 0.6 mmol) and 3-(1-pyrrolidinylmethyl)aniline (134mg, 0.75 mmol) were combined in a vessel with 5 mL isopropanol and 2 drops of 12N HCl. The vessel was sealed and heated with stirring at 95° C. for 18 h. The reaction was cooled to room temperature and the solid was filtered off and washed with isopropanol to give 178 mg (65% yield) of an orange solid as the HCl salt. MS: $M(C_{22}H_{23}ClN_6O)=422.92$, $(M+H)^+=423$ and 425.

EXAMPLES 2-14

The following 2-{[5-chloro-2-(substituted phenylamino)-4-pyrimidinyl]amino}-benzamide compounds were prepared from the corresponding 2-[(2,5-dichloro-4-pyrimidinyl)amino]-benzamide Intermediate 1 and the corresponding aniline following a procedure substantially as described for Example 1.

| Ex. No. | Aryl | Mass (M + H)+ |
|---|---|---|
| 2 | 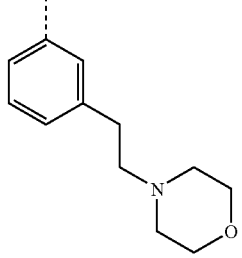 | 453, 455 |
| 3 | (3-morpholinomethyl-phenyl) | 438, 440 |
| 4 | (3-(N-ethyl-N-(2-hydroxyethyl)amino)phenyl) | 440, 442 |
| 5 | (3-(2-(4-acetylpiperazin-1-yl)ethyl)phenyl) | 495, 497 |
| 6 | (3-((4-acetylpiperazin-1-yl)methyl)phenyl) | 479, 481 |
| 7 | (3-(4-methylpiperazin-1-yl)phenyl) | 437, 439 |

-continued

| Ex. No. | Aryl | Mass (M + H)+ |
|---|---|---|
| 8 | 3-((4-methylpiperazin-1-yl)methyl)phenyl | 451, 453 |
| 9 | 4-(N-(5-methylisoxazol-3-yl)sulfamoyl)phenyl | 499, 501 |
| 10 | 4-((methylsulfonyl)methyl)phenyl | 431, 433 |
| 11 | 3-(piperazin-1-ylmethyl)phenyl | 437, 439 |
| 12 | 3-(4-methyl-2-oxopiperazin-1-yl)phenyl | 451, 453 |
| 13 | 3-(2-(piperazin-1-yl)ethyl)phenyl | 452, 454 |

-continued

| Ex. No. | Aryl | Mass (M + H)+ |
|---|---|---|
| 14 | 3-(4-(2-hydroxyethyl)piperazin-1-yl)phenyl | 468, 470 |

INTERMEDIATE 2

2-[(2,5-Dichloro-4-pyrimidinyl)amino]-N-methyl-benzamide

A round-bottomed flask was charged with 2,4,5-trichloropyrimidine (2 g, 11.1 mmol), 2-amino-N-methylbenzamide (2 g, 13.3 mmol), di-isopropyl-ethylamine (2.3 mL, 13.3 mmol) and 40 mL isopropanol. The flask was fitted with a reflux condenser and the reaction was heated to reflux and stirred for 18 h. A white solid appeared in the reaction mixture. The reaction was cooled to room temperature, and the solid was filtered off and washed with isopropanol. After drying, the white solid (3.16 g, 10.5 mmol, 95% yield) was identified as 2-[(2,5-dichloro-4-pyrimidinyl)amino]-N-methylbenzamide. MS: $M(C_{12}H_{10}Cl_2N_4O)=297.14$, $(M+H)^+=$ 297 and 299.

EXAMPLES 15-31

The following 2-{[5-chloro-2-(substituted phenylamino)-4-pyrimidinyl]amino}-N-methylbenzamide compounds were prepared from 2-[(2,5-dichloro-4-pyrimidinyl)amino]-N-methylbenzamide (Intermediate 2) and the corresponding aniline following the procedure substantially as described in Example 1.

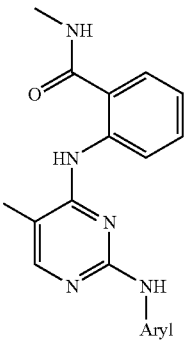

| Ex. No. | Aryl | Mass (M + H)+ |
|---|---|---|
| 15 | 3-(pyrrolidin-1-ylmethyl)phenyl | 437, 439 |
| 16 | 3-(2-morpholinoethyl)phenyl | 466, 468 |
| 17 | 3-(4-methylpiperazin-1-yl)phenyl | 452, 454 |
| 18 | 4-morpholinophenyl | 439, 441 |
| 19 | 3-(4-methyl-2-oxopiperazin-1-yl)phenyl | 466, 468 |
| 20 | 3-(4-morpholinopiperidin-1-yl)phenyl | 522, 524 |
| 21 | 3-(4-methylpiperazin-1-yl)phenyl | 466, 468 |
| 22 | 4-carboxyphenyl | 398, 400 |
| 23 | 4-(morpholinomethyl)phenyl | 467, 469 |
| 24 | 4-(pyrrolidin-1-ylmethyl)phenyl | 437, 439 |
| 25 | 4-(4-isopropylpiperazin-1-yl)phenyl | 480, 482 |
| 26 | 4-(4-methylpiperazin-1-yl)phenyl | 452, 454 |
| 27 | 4-(methylsulfonylmethyl)phenyl | 446, 448 |
| 28 | 4-(2-morpholinoethyl)phenyl | 467, 469 |
| 29 | 2-methoxy-5-(pyrrolidin-1-ylmethyl)phenyl | 467, 469 |
| 30 | 2-methyl-4-(4-methylpiperazin-1-yl)phenyl | 465, 467 |

-continued

| Ex. No. | Aryl | Mass (M + H)+ |
|---|---|---|
| 31 | 4-methoxy-3-(4-methylpiperazin-1-yl)phenyl | 482, 484 |

INTERMEDIATE 3

2-Amino-N-ethylbenzamide

A round-bottomed flask was charged with isatoic anhydride (5.0 g, 0.030 mol), 200 mL water, and 5 mL of methanol. Ethylamine (2N in methanol, 18.4 mL, 0.036 mol) was added slowly to the reaction mixture. After 1 h, the reaction mixture was concentrated to 20 mL. The reaction mixture was acidified with 1N HCl and extracted with EtOAc. The aqueous layer was basified with 6N NaOH and extracted with EtOAc. The EtOAc layer was dried over Na$_2$SO$_4$, filtered, and concentrated to dryness to afford 2-amino-N-ethylbenzamide (4.6 g, 91%): Mass (M+H)+=165.

EXAMPLES 32-34

The following 2-{[5-chloro-2-(substituted phenylamino)-4-pyrimidinyl]amino}-N-ethylbenzamide compounds were prepared from 2-[(2,5-dichloro-4-pyrimidinyl)amino]-N-ethylbenzamide (Intermediate 3) and the corresponding aniline following a procedure substantially as described for the preparation of Example 1.

| Ex. No. | Aryl | Mass (M + H)+ |
|---|---|---|
| 32 | 3-(2-morpholinoethyl)phenyl | 481, 483 |
| 33 | 3-(pyrrolidin-1-ylmethyl)phenyl | 451, 453 |
| 34 | 3-(4-methylpiperazin-1-yl)phenyl | 466, 468 |

INTERMEDIATE 4

2-Amino-N-(1-methylethyl)benzamide

A round-bottomed flask was charged with isatoic anhydride (5.0 g, 0.030 mol) and 30 mL water. Isopropylamine (4.64 mL, 0.049 mol) was added slowly to the reaction mixture. The product precipitated from the reaction mixture. After 1 h, the reaction mixture was filtered and washed with water to give 4.12 g (71% yield) of a white solid

INTERMEDIATE 5

2-[(2,5-Dichloro-4-pyrimidinyl)amino]-N-(1-methylethyl)benzamide

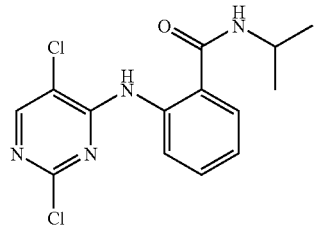

A round-bottomed flask was charged with 2,4,5-trichloropyrimidine (2.0 g, 6.8 mmol), 2-amino-N-(1-methylethyl) benzamide (1.2 g, 7.1 mmol), di-isopropyl-ethylamine (1.4 mL, 8.1 mmol) and 30 mL isopropanol. The flask was fitted with a reflux condenser and the reaction was heated to reflux and stirred for 18 h. A white solid appeared in the reaction mixture. The reaction was cooled to 0° C. and filtered and solid was washed with diethyl ether to afford 2-[(2,5-dichloro-4-pyrimidinyl)amino]-N-(1-methylethyl)benzamide (2.0 g, 90%)

EXAMPLE 35

2-[(5-Chloro-2-{[3-(4-methyl-1-piperazinyl)phenyl]amino}-4-pyrimidinyl)amino]-N-(1-methylethyl)benzamide

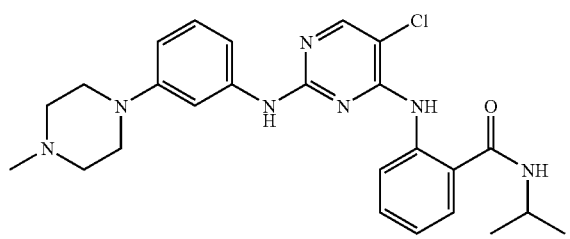

2-[(2,5-Dichloro-4-pyrimidinyl)amino]-N-(1-methylethyl)benzamide (200 mg, 0.61 mmol) and 3-(4-methyl-1-piperazinyl)aniline (117 mg, 0.61 mmol) were combined in a vessel with 8 mL isopropanol and 12N HCl (51 µL, 0.61 mmol). The vessel was sealed and heated with stirring at 95° C. for 18 h. The reaction was cooled to room temperature and the solid was filtered off and washed with diethyl ether to give 120 mg (40%) of an off-white solid as the HCl salt. Mass (M+H)+=480, 481, 482.

EXAMPLES 36-40

The following 2-{[5-chloro-2-(substituted phenylamino)-4-pyrimidinyl]amino}-N-propylbenzamide compounds were prepared from 2-[(2,5-dichloro-4-pyrimidinyl)amino]-N-isopropylbenzamide (Intermediate 5) and the corresponding aniline following a procedure substantially as described for the preparation of Example 33.

| Ex. No. | Aryl | Mass (M + H)+ |
|---|---|---|
| 36 | ![3-(morpholinoethyl)phenyl] | 495, 497 |
| 37 | ![3-(pyrrolidinylmethyl)phenyl] | 465, 467 |
| 38 | ![3-(4-(diethylamino)piperidin-1-yl)phenyl] | 536, 538 |
| 39 | ![3-(4-methylpiperazin-1-yl)phenyl] | 480, 482 |
| 40 | ![2-methyl-4-(4-methylpiperazin-1-yl)phenyl] | 494, 496 |

INTERMEDIATE 6

2-Amino-N-(2-hydroxyethyl)benzamide

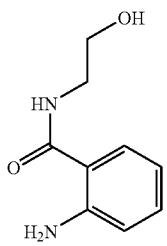

A round-bottomed flask was charged with isatoic anhydride (5.0 g, 0.030 mol) and 40 mL water. Ethanolamine (2.21 mL, 0.036 mol) was added slowly to the reaction mixture. The reaction mixture was acidified with 1N HCl and extracted with EtOAc. The aqueous layer was basified with 6N NaOH and extracted with EtOAc. The EtOac layer was dried over $Na_2SO_4$, filtered, and concentrated to dryness to afford 2-amino-N-(2-hydroxyethyl)benzamide (3.86 g, 70%).

INTERMEDIATE 7

2-[(2,5-Dichloro-4-pyrimidinyl)amino]-N-(2-hydroxyethyl)benzamide

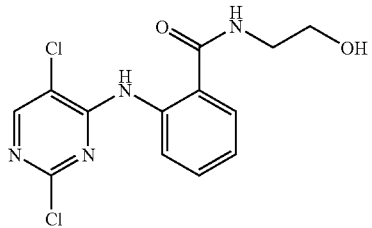

A round-bottomed flask was charged with 2,4,5-trichloropyrimidine (1.3 g, 4.4 mmol), 2-amino-N-(2-hydroxyethyl)benzamide (838 mg, 4.65 mmol), di-isopropyl-ethylamine (925 μL, 5.31 mmol) and 15 mL isopropanol. The flask was fitted with a reflux condenser and the reaction was heated to reflux and stirred for 18 h. A white solid appeared in the reaction mixture. The reaction was cooled to 0° C. and filtered and solid was washed with ether to afford 2-[(2,5-dichloro-4-pyrimidinyl)amino]-N-(2-hydroxyethyl)benzamide (1.3 g, 89%):

EXAMPLE 41

2-[(5-Chloro-2-{[3-(4-methyl-1-piperazinyl)phenyl]amino}-4-pyrimidinyl)amino]-N-(2-hydroxyethyl)benzamide

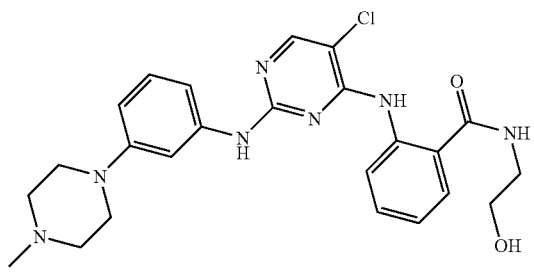

2-[(2,5-Dichloro-4-pyrimidinyl)amino]-N-(2-hydroxyethyl)benzamide (150 mg, 0.45 mmol) and 3-(4-methyl-1-piperazinyl)aniline (87 mg, 0.45 mmol) were combined in a vessel with 8 mL isopropanol and 12N HCl (38 μL, 0.45 mmol). The vessel was sealed and heated with stirring at 95° C. for 18 h. The reaction was cooled to room temperature and the solid was filtered off and washed with ether to give 184 mg (76%) of an off-white solid as the HCl salt. Mass (M+H)+= 482, 484.

EXAMPLES 42-43

The following 2-{[5-chloro-2-(substituted phenylamino)-4-pyrimidinyl]amino}-N-hydroxyethylbenzamide compounds were prepared from 2-[(2,5-dichloro-4-pyrimidinyl)amino]-N-hydroxyethylbenzamide Intermediate 7 and the corresponding aniline following a procedure substantially as described for the preparation of Example 41.

| Ex. No. | Aryl | Mass (M + H)+ |
|---------|------|---------------|
| 42 | ![morpholinoethylphenyl] | 497, 499 |
| 43 | ![pyrrolidinylmethylphenyl] | 467, 469 |

INTERMEDIATE 8

2-Amino-N-(2,2,2-trifluoroethyl)benzamide

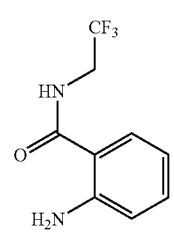

A round-bottomed flask was charged with isatoic anhydride (5.0 g, 0.030 mol), 15 mL water, and triethylamine (4.69 mL, 0.033 mol). (2,2,2-trifluoroethyl)amine hydrochloride (4.98 g, 0.036 mol) was added slowly to the reaction mixture. After 16 h, the reaction mixture was concentrated to dryness. The crude product was purified silica gel column (EtOAc/Hexanes) to afford the title compound as a white solid (3.42 g, 51%): Mass (M+H)+=120, 219.

INTERMEDIATE 9

2-[(2,5-Dichloro-4-pyrimidinyl)amino]-N-(2,2,2-trifluoroethyl)benzamide

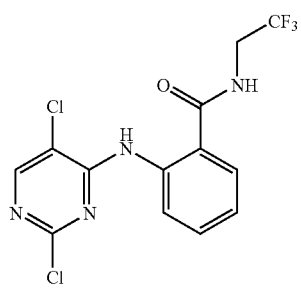

Intermediate 9 was prepared in a similar manner to Intermediate 7.

EXAMPLES 44-46

The following 2-{[5-chloro-2-(substituted phenylamino)-4-pyrimidinyl]amino}-N-trifluoroethylbenzamide compounds were prepared from 2-[(2,5-dichloro-4-pyrimidinyl)amino]-N-trifluoroethylbenzamide Intermediate 9 and the corresponding aniline following a procedure substantially as described for the preparation of Example 41.

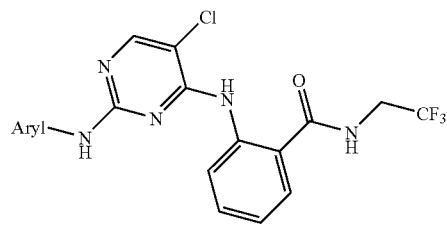

| Ex. No. | Aryl | Mass (M + H)+ |
|---|---|---|
| 44 | ![3-morpholinoethylphenyl] | 535, 537 |
| 45 | ![3-pyrrolidinylmethylphenyl] | 505, 507 |
| 46 | ![3-(4-methylpiperazinyl)phenyl] | 520, 522 |

INTERMEDIATE 10

2-Amino-N-phenylbenzamide

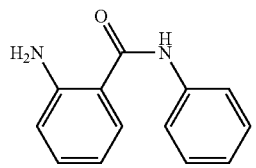

2-Amino-N-phenylbenzamide prepared substantially as described by Dabiri, M.; Salehi, P.; Mohammadi, Ali A.; Baghbanzadeh, M.; Kozehgiry, Gh., *Journal of Chemical Research*, (8), 570-572; 2004.

INTERMEDIATE 11

2-[(2,5-Dichloro-4-pyrimidinyl)amino]-N-phenylbenzamide

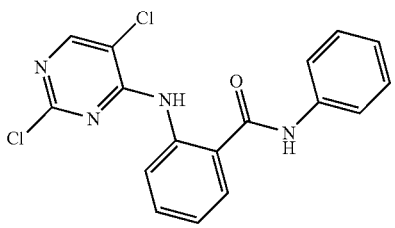

2-[(2,5-Dichloro-4-pyrimidinyl)amino]-N-phenylbenzamide was prepared from 2-amino-N-phenylbenzamide and 2,4,5-trichloropyrimidine using a procedure substantially as described for the preparation of Intermediate 1. Mass (M+H)+=358, 360.

EXAMPLES 47-49

The following 2-{[5-chloro-2-(substituted phenylamino)-4-pyrimidinyl]amino}-N-ethylbenzamide compounds were prepared from 2-[(2,5-dichloro-4-pyrimidinyl)amino]-N-ethylbenzamide Intermediate 11 and the corresponding aniline following the procedure substantially as described for the preparation of Example 1.

| Ex. No. | Aryl | Mass (M + H)+ |
|---|---|---|
| 47 | 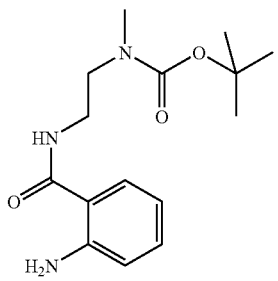 (3-(2-morpholinylethyl)phenyl) | 529, 531 |
| 48 | (3-(pyrrolidin-1-ylmethyl)phenyl) | 499, 501 |
| 49 | (3-(4-methylpiperazin-1-yl)phenyl) | 514, 516 |

INTERMEDIATE 12

1,1-dimethylethyl(2-{[(2-aminophenyl)carbonyl]amino}ethyl)methylcarbamate

A round-bottomed flask was charged with isatoic anhydride (2.0 g, 0.012 mol) and 15 mL water. 1,1-dimethylethyl (2-aminoethyl)methylcarbamate (2.56 g, 0.014 mol) was added slowly to the reaction mixture. The product precipitated from the reaction mixture. After 16 h, the reaction mixture was filtered and washed with water and hexanes to give 3.1 g (86% yield) of a tan solid: Mass (M+H)+=194, 294.

INTERMEDIATE 13

1,1-Dimethylethyl{2-[({2-[(2,5-dichloro-4-pyrimidinyl)amino]phenyl}carbonyl)amino]ethyl}methylcarbamate

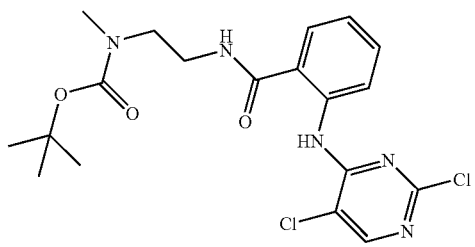

Intermediate 13 was prepared in a similar manner to Intermediate 7.

EXAMPLE 50

2-{[5-Chloro-2-({3-[2-(4-morpholinyl)ethyl]phenyl}amino)-4-pyrimidinyl]amino}-N-[2-(methylamino)ethyl]benzamide

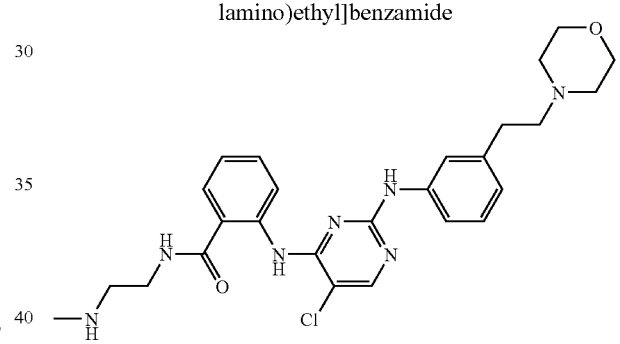

2-{[5-Chloro-2-({3-[2-(4-morpholinyl)ethyl]phenyl}amino)-4-pyrimidinyl]amino}-[2-(methylamino)ethyl]benzamide was prepared from 1,1-dimethylethyl{2-[({2-[(2,5-dichloro-4-pyrimidinyl)amino]phenyl}carbonyl)amino]ethyl}methylcarbamate, Intermediate 13, and the corresponding aniline following the procedure substantially as described for the preparation of Example 41. Mass (M+H)+=510.

INTERMEDIATE 14

2-Amino-N,N-dimethylbenzamide

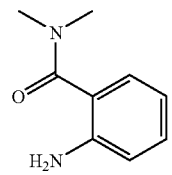

A round bottom flask was charged with 2-nitrobenzoyl-chloride (5 mL, 0.038 mmol) and 150 mL THF. Triethylamine (6 mL, 0.045 mmol) was added followed by dimethylamine (23 mL, 0.045 mmol) and the reaction was stirred at room temperature for 1 h. The reaction was diluted with EtOAC and washed with water and then brine. The organic layer was dried over MgSO4, filtered and concentrated to give a yellow solid (5.4 g): The product was dissolved in 150 mL of EtOH and 10% Pd/C was added. The reaction mixture was placed under 50 psi H$_2$ and shaken in a Parr apparatus. The vessel was refilled until the reaction stopped taking up H$_2$, (~3 refills) and was left shaking overnight. The mixture was filtered through celite and concentrated to give the desired product.

INTERMEDIATE 15

2-[(2,5-Dichloro-4-pyrimidinyl)amino]-N,N-dimethylbenzamide

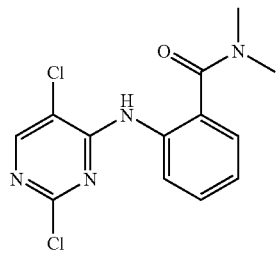

A round-bottomed flask was charged with 2,4,5-trichloropyrimidine (1.0 g, 3.4 mmol), 2-amino-N,N-dimethylbenzamide (587 mg, 3.5 mmol), di-isopropyl-ethylamine (712 µL, 4.08 mmol) and 15 mL of isopropanol. The flask was fitted with a reflux condenser and the reaction was heated to reflux and stirred for 18 h. A white solid appeared in the reaction mixture. The reaction was cooled to 0° C. and filtered and solid was washed with ether to afford 2-[(2,5-dichloro-4-pyrimidinyl)amino]-N,N-dimethylbenzamide (896 mg, 94%):

EXAMPLE 51

2-{[5-Chloro-2-({3-[2-(4-morpholinyl)ethyl]phenyl}amino)-4-pyrimidinyl]amino}-N,N-dimethylbenzamide

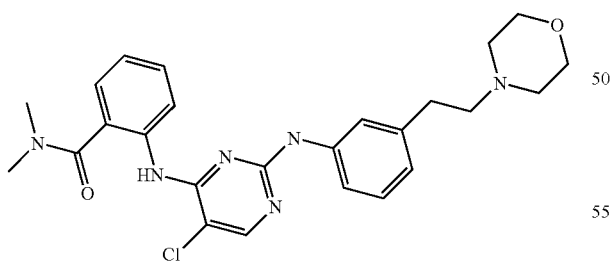

2-[(2,5-dichloro-4-pyrimidinyl)amino]-N,N-dimethylbenzamide (300 mg, 0.96 mmol), 3-[2-(4-morpholinyl)ethyl] aniline (198 mg, 0.96 mmol) were combined in a vessel with 10 mL of isopropanol and TFA (74 µL, 0.96 mmol). The vessel was sealed and heated with stirring at 95° C. for 18 h. The reaction mixture was concentrated to dryness. The crude product was purified via semi-preparative HPLC to afford the title compound as a white solid (83 mg, 18%): Mass (M+H)+= 481, 483.

EXAMPLE 52

2-{[5-Chloro-2-({3-[2-(4-morpholinyl)ethyl]phenyl}amino)-4-pyrimidinyl]amino}-N-{3-[2-(4-morpholinyl)ethyl]phenyl}benzamide

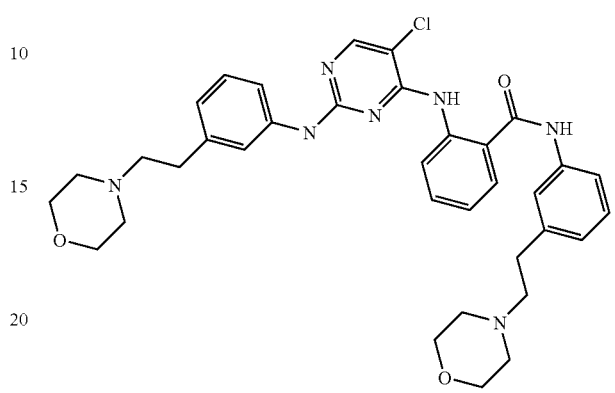

2-[(2,5-Dichloro-4-pyrimidinyl)amino]-N,N-dimethylbenzamide (250 mg, 0.80 mmol), and 3-[2-(4-morpholinyl)ethyl]aniline (165 mg, 0.80 mmol) were combined in a vessel with 10 mL of isopropanol and 12N HCl (67 µL, 0.80 mmol). The vessel was sealed and heated with stirring at 95° C. for 18 h. The reaction mixture was concentrated to dryness. The crude product was purified by HPLC to afford the title compound as a white solid (25 mg, 6%): Mass (M+H)+=642, 644.

EXAMPLES 53-54

The following 2-{[5-nitro-2-(substituted phenylamino)-4-pyrimidinyl]amino}-benzamide compounds were prepared from 2-[(2-chloro-5-nitro-4-pyrimidinyl)amino]benzamide and the corresponding aniline following a procedure substantially as described for the preparation of Example 1. Compounds were isolated by filtration or by evaporation of the reaction mixture and purification by preparative HPLC.

| Ex. No. | Aryl | Mass (M + H)+ |
|---|---|---|
| 53 | 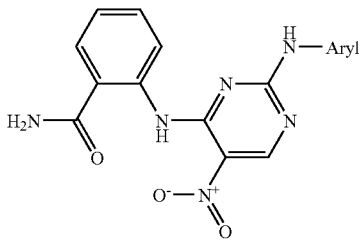 | 464, 465 |

-continued

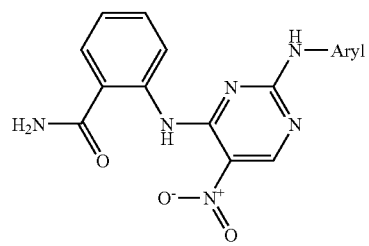

| Ex. No. | Aryl | Mass (M + H)+ |
|---|---|---|
| 54 | (3-pyrrolidin-1-ylmethyl-phenyl) | 434, 435 |

EXAMPLES 55-57

The following 2-{[5-trifluoromethyl-2-(substituted phenylamino)-4-pyrimidinyl]amino}-benzamide compounds were prepared from 2-{[2-chloro-5-(trifluoromethyl)-4-pyrimidinyl]amino}benzamide and the corresponding aniline following the procedure substantially as described for the preparation of Example 1. Compounds were isolated by filtration or by evaporation of the reaction mixture and purification by preparative HPLC.

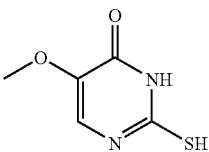

| Ex. No. | Aryl | Mass (M + H)+ |
|---|---|---|
| 55 | (3-(2-morpholinoethyl)phenyl) | 487, 488 |
| 56 | (3-pyrrolidin-1-ylmethyl-phenyl) | 457, 458 |
| 57 | (3-(4-methylpiperazin-1-yl)phenyl) | 472, 473 |

INTERMEDIATE 16

5-(Methoxy)-2-thioxo-2,3-dihydro-4(1H)-pyrimidinone

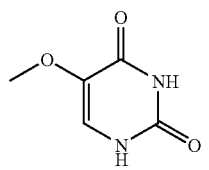

To a three-neck 500 mL round-bottomed flask, equipped with mechanical stirring, were added toluene (100 mL) and metallic sodium (5.75 g; 0.25 moles). A mixture of methyl methoxyacetate (25 mL; 0.25 moles) and ethyl formate (20 mL; 0.25 moles) was added dropwise to the system using an addition funnel. An external water bath was used to keep the system below 30° C. throughout the addition. The system was stirred at room temperature for 16 h. The liquid phase was then decanted and the remaining gummy solid was treated with thiourea (19 g; 0.25 moles) and ethanol (50 mL). The system was heated to reflux for 4 h and cooled to room temperature. The light pink solid was collected by filtration and dissolved in 125 mL of water. The solution was acidified (pH 4-5) with concentrated HCl. The solid precipitated was collected by filtration, washed with water and dried under high vacuum Intermediate 16 (22 g; 56% yield) was obtained. MS: $(M+H)^+=159$.

INTERMEDIATE 17

5-(Methoxy)-2,4(1H,3H)-pyrimidinedione

A mixture of 5-(methoxy)-2-thioxo-2,3-dihydro-4(1H)-pyrimidinone (21.5 g; 0.137 moles), chloroacetic acid (21.5 g; 0.227 moles), and water (585 mL) was refluxed for 2 h. Concentrated HCl (85 mL) was added and the mixture was then refluxed for 16 h. Upon cooling, a solid formed and was collected by filtration, washed with water and dried to yield the desired product (18.2 g; 94% yield). MS: $(M+H)^+=143$.

INTERMEDIATE 18

2,4-Dichloro-5-(methoxy)pyrimidine

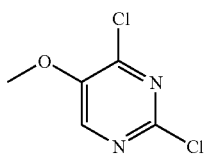

5-(Methoxy)-2,4(1H,3H)-pyrimidinedione (18 g; 0.128 moles), phosphorous oxychloride (90 mL) and dimethylaniline (18 mL) were heated to reflux for 2 h. The system was cooled to room temperature and carefully poured over ice. The white solid formed was separated by filtration. The aqueous filtrate was extracted with diethyl ether (4×). The ether layers were combined and dried over anhydrous sodium sulfate. Removal of the solvent in vacuo afforded Intermediate 18 (6 g; 40% yield based on recovered starting material). MS: $(M+H)^+$=179, 181 and 183.

INTERMEDIATE 19

2-{[2-Chloro-5-(methoxy)-4-pyrimidinyl]amino}benzamide

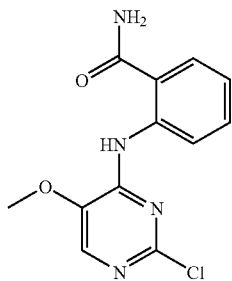

2,4-Dichloro-5-(methoxy)pyrimidine (1.5 g; 8.43 mmoles), the aniline 2-aminobenzamide (1.15 g; 8.43 mmoles), diethylisopropylamine (4 mL) and n-butanol (25 mL) were refluxed for 16 h. Upon cooling to room temperature, product crystallized. The white solid was collected by filtration, washed with cold n-butanol and cold hexane. The solid was dried under high vacuum affording Intermediate 19 (1.1 g; 50% yield). MS: $(M+H)^+$=279 and 281.

INTERMEDIATE 20

2-{[2-Chloro-5-(methoxy)-4-pyrimidinyl]amino}-N-methyl-benzamide

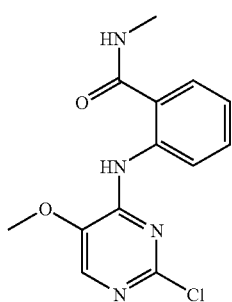

2-{[2-Chloro-5-(methoxy)-4-pyrimidinyl]amino}-N-methyl-benzamide (1.5 g; 60%) was prepared following a procedure substantially as described for the preparation of Intermediate 19, using 2-amino-N-methyl-benzamide as the aniline. MS: $(M+H)^+$=293 and 295.

INTERMEDIATE 21

2-{[2-Chloro-5-(methoxy)-4-pyrimidinyl]amino}-N-isopropyl-benzamide

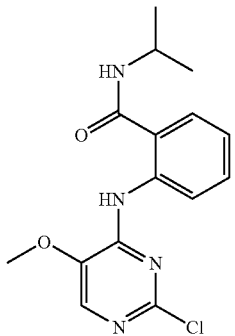

2-{[2-Chloro-5-(methoxy)-4-pyrimidinyl]amino}-N-isopropyl-benzamide (1.4 g; 52%) was prepared following a procedure substantially as described for the preparation of Intermediate 19, using 2-amino-N-isopropyl-benzamide as the aniline. MS: $(M+H)^+$=321 and 323.

EXAMPLE 58

2-{[5-(Methoxy)-2-({3-[2-(4-morpholinyl)ethyl]phenyl}amino)-4-pyrimidinyl]amino}benzamide

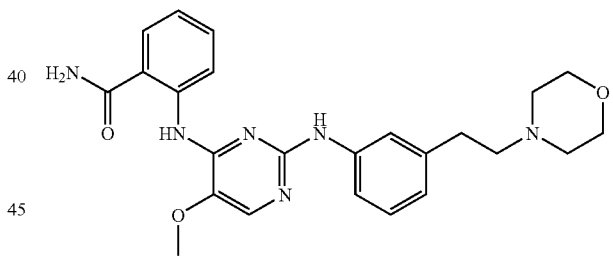

3-[2-(4-Morpholinyl)ethyl]aniline (103 mg; 0.5 mmoles) was dissolved in THF (2 mL) and treated with 1 mL of a solution of 1M HCl in ethyl ether. The mixture was stirred for 5 min and then concentrated in vacuo. The residue was treated with 2-{[2-chloro-5-(methoxy)-4-pyrimidinyl]amino}benzamide (139 mg; 0.5 mmoles) and isopropanol (4 mL). The suspension was stirred in a vial, which was sealed and heated at 100° C. for 24 h. Upon cooling, the solid was collected by filtration, washed with cold isopropanol and dried in vacuo to afford the desired product. MS: $(M+H)^+$=449.

EXAMPLES 59-67

Examples 59-67 were prepared from Intermediates 19-21 and the corresponding aniline following a procedure substantially as described for the preparation of Example 58. Intermediate 19 was used for the synthesis of 2-{[5-methoxy-2-(substituted phenylamino)-4-pyrimidinyl]amino}- benzamides. Intermediate 20 was used for the synthesis of 2-{[5-methoxy-2-(substituted phenylamino)-4-pyrimidinyl]amino}-N-methyl-benzamides. Intermediate 21 was used for the synthesis of 2-{[5-methoxy-2-(substituted phenylamino)-4-pyrimidinyl]amino}-N-isopropyl-benzamides.

| Ex. No. | R¹ | Aryl | Mass (M + H)+ |
|---|---|---|---|
| 59 | H | 3-(4-methylpiperazin-1-yl)-4-methoxyphenyl | 464 |
| 60 | H | 4-(4-methylpiperazin-1-yl)phenyl | 434 |
| 61 | H | 4-(4-methylpiperazin-1-yl)-3-methylphenyl | 448 |
| 62 | Me | 4-(4-methylpiperazin-1-yl)phenyl | 448 |
| 63 | Me | 4-(4-methylpiperazin-1-yl)-3-methylphenyl | 462 |
| 64 | iPr | 3-(2-morpholinoethyl)phenyl | 491 |
| 65 | iPr | 3-(4-methylpiperazin-1-yl)-4-methoxyphenyl | 506 |
| 66 | iPr | 4-(4-methylpiperazin-1-yl)phenyl | 476 |

-continued

| Ex. No. | R¹ | Aryl | Mass (M + H)+ |
|---|---|---|---|
| 67 | iPr | 4-(4-methylpiperazin-1-yl)-3-methylphenyl | 490 |

EXAMPLES 68-70

The following 2-{[5-fluoro-2-(substituted phenylamino)-4-pyrimidinyl]amino}-benzamide compounds were prepared from 2-{[2-chloro-5-fluoro-4-pyrimidinyl]amino}benzamide and the corresponding aniline following a procedure substantially as described for the preparation of Example 1. Product was isolated by filtration or by evaporation of the reaction mixture and purification by preparative HPLC.

| Ex. No. | Aryl | Mass (M + H)+ |
|---|---|---|
| 68 | 3-(4-methylpiperazin-1-yl)phenyl | 422, 423 |
| 69 | 3-(pyrrolidin-1-ylmethyl)phenyl | 407, 408 |

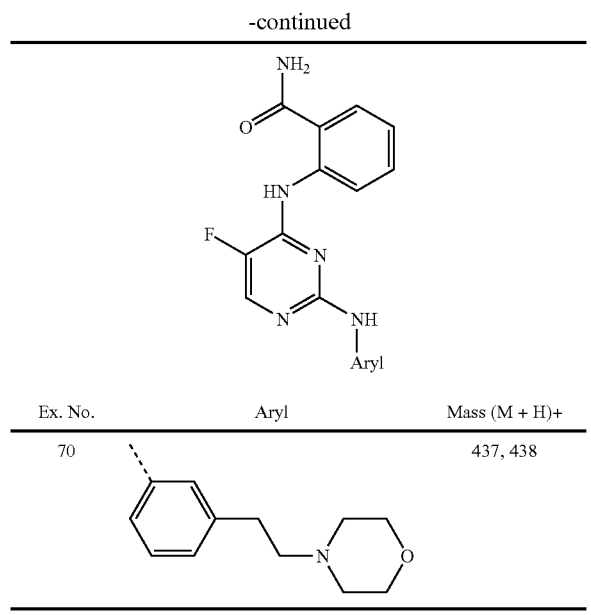

| Ex. No. | Aryl | Mass (M + H)+ |
| --- | --- | --- |
| 70 | (3-(2-morpholinoethyl)phenyl) | 437, 438 |

EXAMPLES 71-74

The following 2-{[5-fluoro-2-(substituted phenylamino)-4-pyrimidinyl]amino}-N-methylbenzamide compounds were prepared from 2-[(2-chloro-5-fluoro-4-pyrimidinyl)amino]-N-methylbenzamide and the corresponding aniline following a procedure substantially as described for the preparation of Example 1. Product was isolated by filtration or by evaporation of the reaction mixture and purification by preparative HPLC.

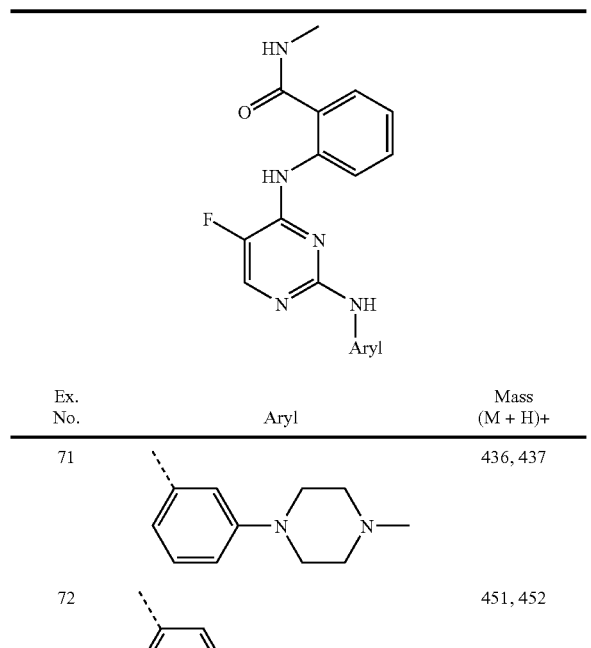

| Ex. No. | Aryl | Mass (M + H)+ |
| --- | --- | --- |
| 71 | (3-(4-methylpiperazin-1-yl)phenyl) | 436, 437 |
| 72 | (3-(2-morpholinoethyl)phenyl) | 451, 452 |

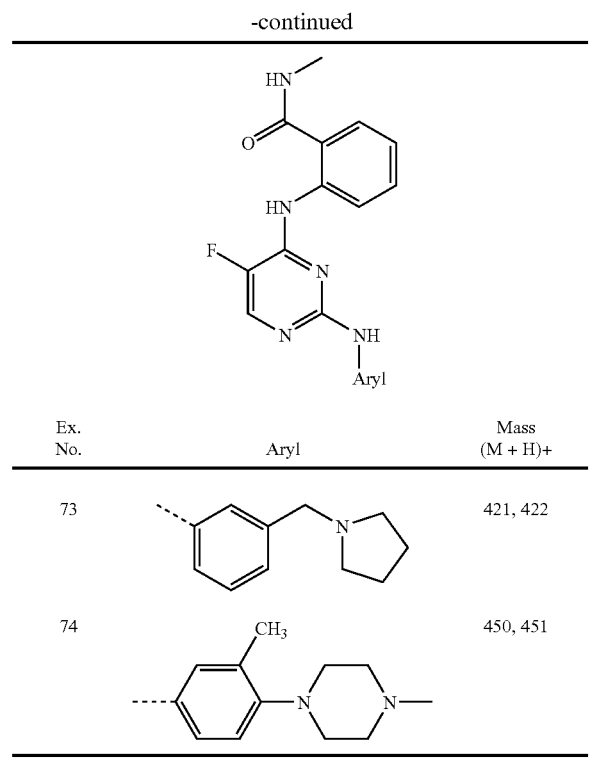

| Ex. No. | Aryl | Mass (M + H)+ |
| --- | --- | --- |
| 73 | (3-(pyrrolidin-1-ylmethyl)phenyl) | 421, 422 |
| 74 | (3-methyl-4-(4-methylpiperazin-1-yl)phenyl) | 450, 451 |

EXAMPLE 75

2-[(5-Fluoro-2-{[3-methyl-4-(4-methyl-1-piperazinyl)phenyl]amino}-4-pyrimidinyl)amino]-N-(1-methylethyl)benzamide

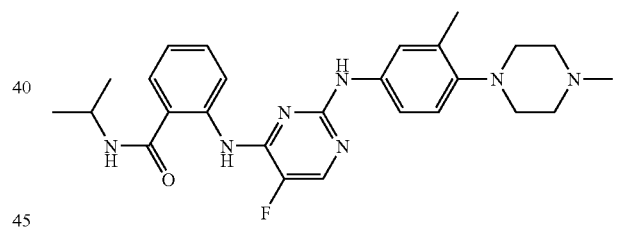

2-[(2-Chloro-5-fluoro-4-pyrimidinyl)amino]-N-(1-methylethyl)benzamide (75 mg, 0.24 mmol) and the pre-formed HCl salt of 3-methyl-4-(4-methyl-1-piperazinyl)aniline (49 mg, 0.24 mmol) were combined in a vessel with 3 mL isopropanol. The vessel was sealed and heated with stirring at 110° C. for 72 h. The reaction was cooled to room temperature and the solvent was removed. Purification by reverse phase preparative HPLC afforded 28 mg (24% yield) of tan solid. The solid was dissolved in THF to which 1 eq of 1M HCl Ether was added and the resultant white solid was filtered off to afford the HCl salt. MS: $M(C_{26}H_{32}FN_7O)=477.58$, $(M+H)^+=478.2$ and 479.2.

EXAMPLES 76-79

The following 2-{[5-fluoro-2-(substituted phenylamino)-4-pyrimidinyl]amino}-N-(1-methylethyl)benzamide compounds were prepared from 2-[(2-chloro-5-fluoro-4-pyrimidinyl)amino]-N-(1-methylethyl)benzamide and the corresponding aniline following a procedure substantially as described for the preparation of Example 1. Product was isolated by filtration or by evaporation of the reaction mixture and purification by preparative HPLC.

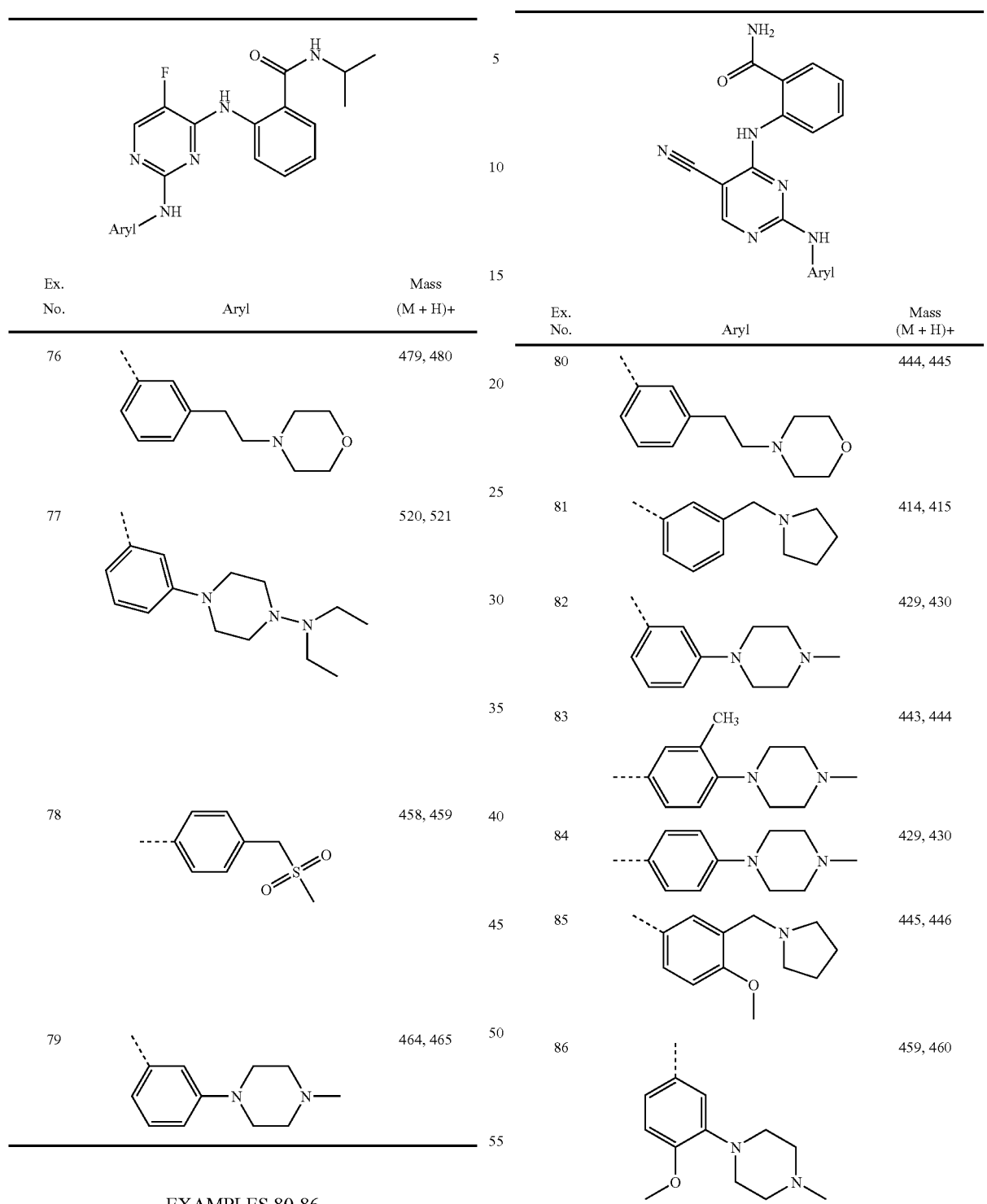

EXAMPLES 80-86

The following 2-{[5-cyano-2-(substituted phenylamino)-4-pyrimidinyl]amino}-benzamide compounds were prepared from 2-{[2-chloro-5-cyano-4-pyrimidinyl]amino}benzamide and the corresponding aniline following a procedure substantially as described for Example 1. Product was isolated by filtration or by evaporation of the reaction mixture and purification by preparative HPLC.

EXAMPLES 87-89

The following 2-{[5-methyl-2-(substituted phenylamino)-4-pyrimidinyl]amino}-benzamide compounds were prepared from 2-{[2-chloro-5-methyl-4-pyrimidinyl]amino}benzamide and the corresponding aniline following a procedure substantially as described for Example 1. Compounds were isolated by filtration or by evaporation of the reaction mixture and purification by preparative HPLC.

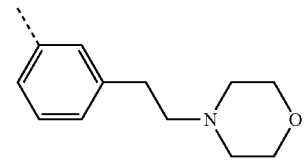

| Ex. No. | Aryl | Mass (M + H)+ |
|---|---|---|
| 87 | 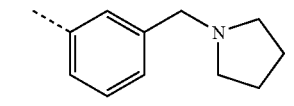 | 433, 434 |
| 88 | 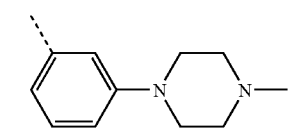 | 403, 404 |
| 89 | 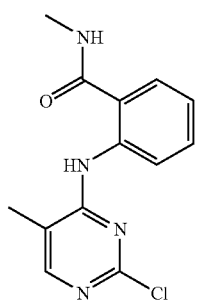 | 418, 419 |

INTERMEDIATE 22

2-[(2-Chloro-5-methyl-4-pyrimidinyl)amino]-N-methylbenzamide

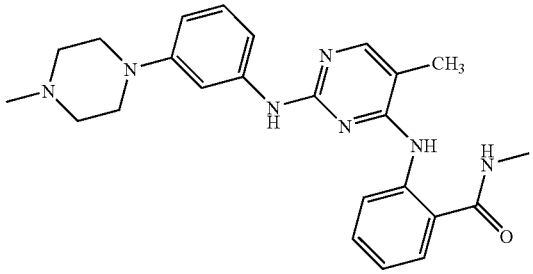

A vessel was charged with 2,4-dichloro-5-methylpyrimidine (10 g, 61.3 mmol), 2-amino-N-methylbenzamide (9.2 g, 61.3 mmol), di-isopropyl-ethylamine (21 mL, 122 mmol) and 50 mL n-butanol. The vessel was sealed and heated with stirring at 95° C. for 18 h. The reaction was cooled to room temperature whereupon a white solid precipitated. The solid was filtered off and washed with cold isopropanol. Then, one-third of the volume of the filtrate was removed in vacuo and the concentrated mother liquor was heated and cooled as before to produce additional solid material. After drying, the total white solid (9.04 g, 32.8 mmol, 53% yield) was identified as 2-[(2-chloro-5-methyl-4-pyrimidinyl)amino]-N-methylbenzamide. MS: $M(C_{13}H_{13}ClN_4O)=276.73$, $(M+H)^+=277$ and 278.

EXAMPLE 90

N-Methyl-2-[(5-methyl-2-{[3-(4-methyl-1-piperazinyl)phenyl]amino}-4-pyrimidinyl)amino]benzamide

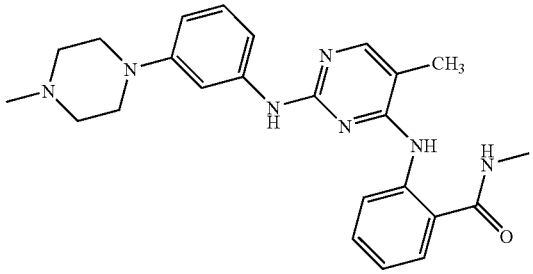

2-[(2-Chloro-5-methyl-4-pyrimidinyl)amino]-N-methylbenzamide (200 mg, 0.72 mmol) and 3-(4-methyl-1-piperazinyl)aniline (142 mg, 0.72 mmol) were combined in a vessel with 5 mL of isopropanol and 2 drops of 12N HCl. The vessel was sealed and heated with stirring at 95° C. for 18 h. The reaction was cooled to room temperature and the solid was filtered off and washed with isopropanol to give the HCl salt of the desired product (206 mg, 66% yield). MS: $M(C_{24}H_{29}ClN_7O)=431.54$, $(M+H)^+=432$ and 433.

EXAMPLES 91-97

The following 2-{[5-methyl-2-(substituted phenylamino)-4-pyrimidinyl]amino}-benzamide compounds were prepared from 2-{[2-chloro-5-methyl-4-pyrimidinyl]amino}benzamide and the corresponding aniline following a procedure substantially as used for the preparation of Example 90. Product was isolated by filtration or by evaporation of the reaction mixture and purification by preparative HPLC.

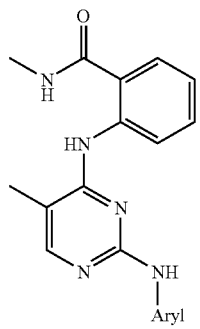

| Ex. No. | Aryl | Mass (M + H)+ |
|---|---|---|
| 91 | | 446 |
| 92 | | 432 |
| 93 | | 426 |
| 94 | | 419 |
| 95 | | 445 |
| 96 | | 462 |
| 97 | | 426 |

EXAMPLE 98 (PROCEDURE I)

N-(1-Methylethyl)-2-[(5-methyl-2-{[3-(4-methyl-2-oxo-1-piperazinyl)phenyl]amino}-4-pyrimidinyl)amino]benzamide

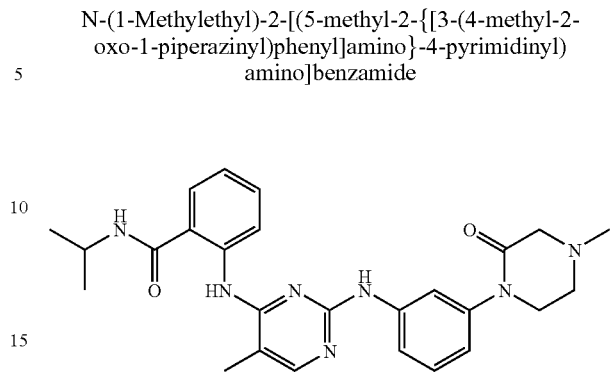

A. Preparation of 1-(3-aminophenyl)-4-methyl-2-piperazinone

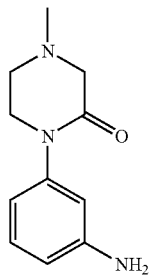

3-Nitroaniline (20.0 g, 145 mmol) was combined with EtOAc (120 mL) and 20% aq potassium bicarbonate (100 mL) in a vessel to form a biphasic solution, which was cooled to 0° C. and stirred. Chloroacetyl chloride (11 mL, 145 mmol) was added dropwise over 30 min, after which time the reaction mixture was warmed to room temperature and stirred for an additional 30 min. The aqueous layer was removed, after which ethanolamine (34 mL, 435 mmol) was added to the organic layer. The mixture was heated to 60° C. for 3 h, then water (60 mL) was added and the solution reheated to 60° C. and then cooled. The aqueous layer was removed and the organic layer was washed with brine (3×60 mL). The solvent was removed and the resulting yellow solid was combined with stirring with 30% EtOAc in hexane (100 mL). The solid was collected by filtration and washed with additional solvent (3×70 mL of 30% EtOAc in hexane). The off-white solid was collected and dried in vacuo over night. This compound was identified as $N^2$-(2-hydroxyethyl)-$N^2$-methyl-$N^1$-(3-nitrophenyl)glycinamide, which was used in the next step without further purification. (28.68 g 78% yield) 1H NMR (400 MHz, DMSO-$d_6$) δ ppm 10.28 (1H, br. s.) 8.69 (1H, t, J=2.15 Hz) 8.01 (1H, dt, J=7.07, 1.01 Hz) 7.93 (1H, dt, J=8.27, 1.17 Hz) 7.62 (1H, t, J=8.21 Hz) 4.82 (1H, br. s.) 3.53 (2H, br. s.) 3.33 (1H, s) 3.24 (2H, s) 2.55 (2H, t, J=5.56 Hz) 2.34 (3H, s).

A solution of diisopropyl azodicarboxylate (51.4 mmol, 1.3 eq) in EtOAc (20 mL) was added to $N^2$-(2-hydroxyethyl)-$N^2$-methyl-$N^1$-(3-nitrophenyl)glycinamide (10 g, 39.5 mmol) and tributylphosphine (13 mL, 51.4 mmol, 1.3 eq.) in EtOAc (50 mL) over a 60-min period during which time the internal reaction temperature was maintained between 25° C. and 30° C. Ethanolic HCl (2.0 M solution, 20 mL) was added dropwise and the resulting slurry was cooled to 0° C. and stirred for an additional hour. The solid was collected by filtration, washed with isopropanol and dried in vacuo at 40° C. for 18 h to give the desired 1-methyl-4-(3-nitrophenyl) piperazine, which was used in the next step without further purification (8.43 g, 79% yield) 1H NMR (400 MHz, DMSO-$d_6$) δ ppm 11.90 (1H, br s) 8.28 (1H, t, J=2.15 Hz) 8.20 (1H, ddd, J=8.08, 2.27, 1.01 Hz) 7.85 (1H, d, J=2.02 Hz) 7.84 (1H, d, J=2.02 Hz) 7.77 (1H, t, J=8.08 Hz) 4.04 (3H, br. s.) 3.66 (1H, br. s.) 3.56 (1H, br. s.) 2.92 (4H, s).

Pd/C (10%, 420 mg) was added to a solution of 1-methyl-4-(3-nitrophenyl)piperazine (8.4 g) in methanol (500 mL) and water (20 mL). The reaction mixture was stirred and degassed with nitrogen, and the vessel was charged with $H_2$ gas at atmospheric pressure. The reaction was allowed to proceed overnight after which time the Pd/C was removed by filtration over celite and the methanol and water were removed in vacuo to give 1-(3-aminophenyl)-4-methyl-2-piperazinone as a yellow solid (7.08 g, 95% yield). 1H NMR (400 MHz, DMSO-$d_6$) δ ppm 7.07 (1H, t, J=7.83 Hz) 6.48-6.55 (2H, m) 6.46 (1H, d, J=1.01 Hz) 6.44 (1H, s) 3.88 (4H, s) 3.54 (2H, br. s.) 2.82 (3H, s)

B. Preparation of 2-[(2-chloro-5-methyl-4-pyrimidinyl)amino]-N-(1-methyethyl)benzamide

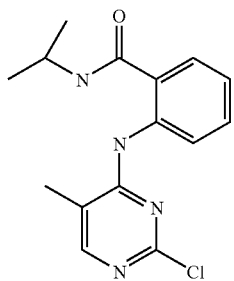

A vessel was charged with 2,4-dichloro-5-methylpyrimidine (5.0 g, 28 mmol), 2-amino-N-(1-methyethyl)benzamide (5.46 g, 34.3 mmol), di-isopropyl-ethylamine (7.0 mL, 42 mmol) and 2-(methyloxy)ethanol (30 mL) and sealed and heated with stirring at 130° C. for 36 hours. The reaction was cooled to room temperature and 50 mL water was added dropwise to afford a milky white solution, which was heated to 100° C. to induce precipitation. The solution was cooled and the solid collected by filtration. The collected solid was washed successively with water (2×50 mL) and hexane (3×50 mL). After drying, a white solid was collected (6.56 g, 77% yield) and identified as 2-[(2-chloro-5-methyl-4-pyrimidinyl)amino]-N-(1-methyethyl)benzamide. 1H NMR (400 MHz, DMSO-$d_6$) δ ppm 11.51 (1H, s) 8.56-8.63 (2H, m) 8.15 (1H, s) 7.81 (1H, dd, J=7.83, 1.52 Hz) 7.58 (1H, dd, J=15.66, 1.52 Hz) 7.17 (1H, dd, J=15.28, 1.14 Hz) 4.13 (1H, dd, J=14.02, 6.69 Hz) 2.18 (3H, s) 1.18 (6H, d, J=6.57 Hz).

C. Preparation of N-(1-methylethyl)-2-[(5-methyl-2-{[3-(4-methyl-2-oxo-1-piperazinyl)phenyl]amino}-4-pyrimidinyl)amino]benzamide 2-[(2-Chloro-5-methyl-4-pyrimidinyl)amino]-N-(1-methylethyl)benzamide (103 mg, 0.337 mmol) and 1-(3-aminophenyl)-4-methyl-2-piperazinone (68.8 mg, 0.335 mmol) were stirred at 95° C. overnight in isopropanol (10 mL) with 12 N HCl (0.056 mL, 0.673 mmol). The reaction was cooled to room temperature and the solid was filtered off and washed with isopropanol. The solid was chromatographed using reverse phase HPLC eluting with 5-30% acetonitrile containing 0.1% formic acid to give a white solid (43 mg, 27%) after lyophilozation of the combined HPLC fractions. MS: $M(C_{26}H_{31}N_7O_2)$=473.57, $(M+H)^+$=473.8.

EXAMPLE 98 (PROCEDURE II) AND HCL SALT

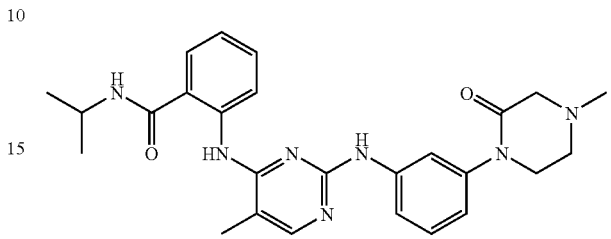

A. N-(1-Methylethyl)-2-[(5-methyl-2-{[3-(4-methyl-2-oxo-1-piperazinyl)phenyl]amino}-4-pyrimidinyl)amino] benzamide was also synthesized as follows: To a solution of 2-[(2-chloro-5-methyl-4-pyrimidinyl)amino]-N-(1-methyl-ethyl)benzamide (16.6 g, 55 mmol) and the hydrochloride salt of 1-(3-aminophenyl)-4-methyl-2-piperazinone (14.5 g, 60 mmol) in isopropanol (500 mL) was added 6N HCl (1 mL). The reaction was heated under reflux for 14 h, then treated with 500 mL of water and neutralized with 1 M NaOH to pH ~9. The organics were extracted with dichloromethane (2×300 mL) and the extracts were combined, washed with brine, and dried over $MgSO_4$. The solution was then filtered and evaporated. Product was purified by normal phase chromatography (dichloromethane:methanol 2% to 15% over 60 mins). After solvent evaporation, product was recrystallized from acetonitrile (18 g, 38 mmol, 69% yield). MS: $M(C_{26}H_{31}N_7O_2)$=473.57, $(M+H)^+$=473.8. 1H NMR (400 MHz, MeOD) δ ppm 1.24 (d, J=6.57 Hz, 6H) 2.18 (s, 3H) 2.42 (s, 3H) 2.74-2.85 (m, 2H) 3.25 (s, 2 H) 3.58-3.74 (m, 2H) 4.08-4.30 (m, 1H) 6.88 (dd, J=7.96, 1.14 Hz, 1H) 7.07-7.17 (m, 1H) 7.31 (t, J=8.08 Hz, 1H) 7.42-7.54 (m, 2H) 7.67 (dd, J=7.83, 1.26 Hz, 1H) 7.71 (t, J=2.02 Hz, 1H) 7.90 (s, 1H) 8.51-8.67 (m, 1H).

B. The HCl Salt was Prepared as Follows:

To a suspension of N-(1-methylethyl)-2-[(5-methyl-2-{[3-(4-methyl-2-oxo-1-piperazinyl)phenyl]amino}-4-pyrimidinyl)amino]benzamide (7.2 g, 15.2 mmol) in methanol (200 mL) was added HCl (2 M solution in diethyl ether, 7.6 mL, 15.2 mmol). After 30 mins, the solution was filtered to remove any floating solids, and the and filtrate was concentrated in vacuo. The hydrochloride salt of the product was dried overnight (7.7 g, 98% yield). 1H NMR (400 MHz, MeOD) δ ppm 1.25 (d, J=6.57 Hz, 6H) 2.26 (s, 3H) 2.86 (s, 3H) 3.44 (t, J=5.31 Hz, 2H) 3.84 (s, 2H) 3.92 (t, J=5.56 Hz, 2H) 4.15-4.29 (m, 1H) 7.25-7.34 (m, 2H) 7.43-7.59 (m, 4H) 7.73-7.80 (m, 2H) 8.38 (d, J=7.83 Hz, 1H) 8.44 (d, J=8.34 Hz, 1H).

EXAMPLES 99-102

The following 2-{[5-isopropyl-2-(substituted phenylamino)-4-pyrimidinyl]amino}-benzamide compounds were prepared from 2-{[2-chloro-5-isopropyl-4-pyrimidinyl] amino}benzamide and the corresponding aniline using a procedure substantially as described for the preparation of Example 98 Procedure I. Product was isolated by filtration or by evaporation of the reaction mixture and purification by preparative HPLC.

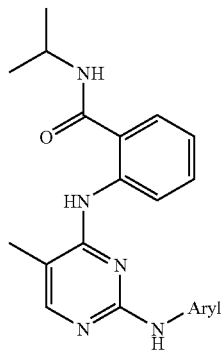

| Ex. No. | Aryl | Mass (M + H)+ |
|---|---|---|
| 99 | 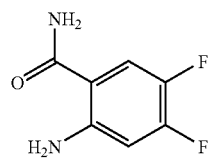 | 460 |
| 100 | | 453 |
| 101 | | 490 |
| 102 | | 474 |

INTERMEDIATE 23

2-Amino-4,5-difluorobenzamide

A round-bottomed flask was charged with 2-amino-4,5-difluorobenzoic acid (2 g, 11.7 mmol) and 50 mL tetrahydrofuran (THF). The flask was cooled to 0° C., whereupon a 20% solution of phosgene (6.11 mL, 11.7 mmol) in toluene was added dropwise. The reaction was stirred for 15 min at 0° C., after which a large stoichiometric excess of ammonium hydroxide was added. The reaction was then warmed to room temperature, stirred for 18 h, then washed with water, and then extracted three times with ethyl acetate. Organic layers were combined and dried over sodium sulfate, then concentrated. The product was identified as 2-amino-4,5-difluorobenzamide (1.24 g, 7.2 mmol, 62% yield). MS: $M(C_7H_6F_2N_2O)=172.13$, $(M+H)^+=173.2$.

INTERMEDIATE 24

2-Amino-4,5-difluoro-N-methylbenzamide

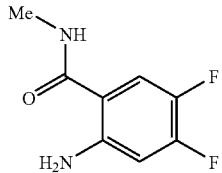

2-Amino-4,5-difluoro-N-methylbenzamide was prepared using a procedure substantially as described for the preparation of Intermediate 23. In this case, methyl amine was used to form the amide. Mass (M+H)+=187.

INTERMEDIATE 25

2-Amino-6-fluoro-N-methylbenzamide

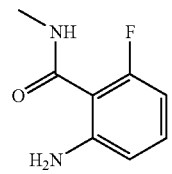

A round-bottomed flask was charged with 5-fluoro-2H-3,1-benzoxazine-2,4(1H)-dione (500 mg, 2.8 mmol) and 30 mL water. The reaction was stirred for 15 min and then methylamine was added. The reaction was then stirred for 2 h. It was then extracted three times with ethyl acetate. Organic layers were combined and dried over sodium sulfate, then concentrated. The product was identified as 2-amino-6-fluoro-N-methylbenzamide (365 mg, 2.4 mmol, 86% yield). MS: $M(C_8H_9FN_2O)=168.17$, $(M+H)^+=169.3$.

INTERMEDIATE 26

2-Amino-6-fluoro-N-(1-methylethyl)benzamide

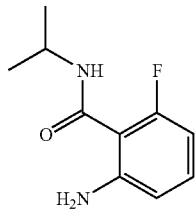

2-Amino-6-fluoro-N-(1-methylethyl)benzamide was prepared from 5-fluoro-2H-3,1-benzoxazine-2,4(1H)-dione and 'isopropyl amine following a procedure substantially as described for the preparation of Intermediate 25. MS: (M+H)+=197.

INTERMEDIATE 27

2-[(2,5-Dichloro-4-pyrimidinyl)amino]-4,5-difluorobenzamide

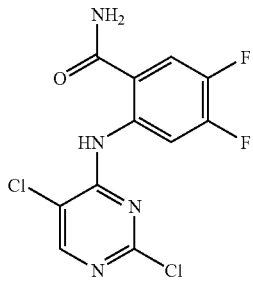

A round-bottomed flask was charged with 2,4,5-trichloropyrimidine (1.17 g, 6.4 mmol), 2-amino-4,5-difluorobenzamide (1.0 g, 5.8 mmol), di-isopropyl-ethylamine (5.06 mL, 29.0 mmol) and 50 mL of isopropanol. The flask was fitted with a reflux condenser and the reaction was heated to reflux and stirred for 18 h. A white solid appeared in the reaction mixture. The reaction was cooled to room temperature, one-third of the volume was removed in vacuo, and the solid was filtered off and washed with isopropanol. After drying, the white solid (1.45 g, 4.5 mmol, 78% yield) was identified as 2-[(2,5-dichloro-4-pyrimidinyl)amino]-4,5-difluorobenzamide. MS: M($C_{11}H_6Cl_2F_2N_4O$)=319.10, (M+H)$^+$=319.2.

Intermediates 28-31

The following 2-[(2,5-dichloro-4-pyrimidinyl)amino]-fluorobenzamide compounds were prepared from the corresponding 2-aminofluorobenzamide and 2,4,5-trichloropyrimidine following a procedure substantially as described for Intermediate 27.

| Int. No. | Structure | Mass (M + H)+ |
|---|---|---|
| 28 | 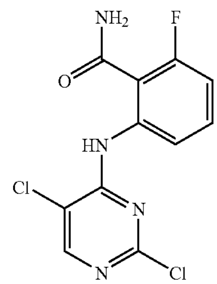 | 301 |
| 29 | 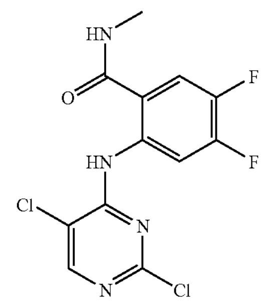 | 333 |
| 30 | 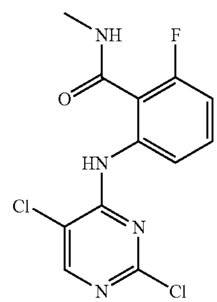 | 315 |
| 31 | 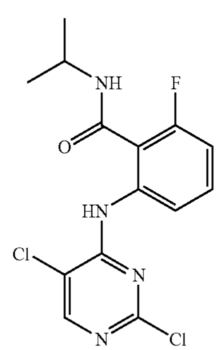 | 343 |

EXAMPLES 103-107

The following 2-{[5-chloro-2-(substituted phenylamino)-4-pyrimidinyl]amino}-4,5-difluorobenzamide compounds were prepared from the corresponding 2-[(2,5-dichloro-4-pyrimidinyl)amino]-4,5-difluoro-benzamide Intermediate 27 and the corresponding aniline following a procedure substantially as described for the preparation of Example 1.

| Ex. No. | Aryl | Mass (M + H)+ |
|---|---|---|
| 103 | 3-(pyrrolidin-1-ylmethyl)phenyl | 459 |
| 104 | 3-(2-morpholinoethyl)phenyl | 489 |
| 105 | 3-(4-methylpiperazin-1-yl)phenyl | 474 |
| 106 | 3-((4-methylpiperazin-1-yl)methyl)phenyl | 488 |
| 107 | 4-((methylsulfonyl)methyl)phenyl | 468 |

| Ex. No. | Aryl | Mass (M + H)+ |
|---|---|---|
| 108 | 3-(2-morpholinoethyl)phenyl | 503 |
| 109 | 3-(4-methylpiperazin-1-yl)phenyl | 488 |
| 110 | 3-(4-methyl-3-oxopiperazin-1-yl)phenyl | 502 |
| 111 | 4-((methylsulfonyl)methyl)phenyl | 482 |
| 112 | 2-methoxy-5-(pyrrolidin-1-ylmethyl)phenyl | 503 |
| 113 | 4-(4-methylpiperazin-1-yl)phenyl | 488 |
| 114 | 2-methoxy-5-(4-methylpiperazin-1-yl)phenyl | 518 |
| 115 | 2-methyl-4-(4-methylpiperazin-1-yl)phenyl | 502 |

EXAMPLES 108-116

The following 2-{[5-chloro-2-(substituted phenylamino)-4-pyrimidinyl]amino}-4,5-difluoro-N-methylbenzamide compounds were prepared from the corresponding 2-[(2,5-dichloro-4-pyrimidinyl)amino]-4,5-difluoro-N-methylbenzamide Intermediate 29 and the corresponding aniline following a procedure substantially as described for the preparation of Example 1.

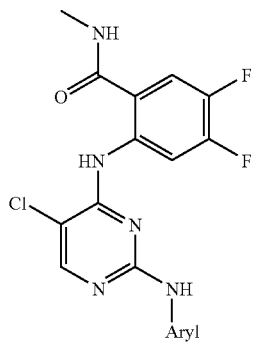

| Ex. No. | Aryl | Mass (M + H)+ |
|---|---|---|
| 116 | | 516 |

EXAMPLES 117-119

The following 2-{[5-chloro-2-(substituted phenylamino)-4-pyrimidinyl]amino}-6-fluorobenzamide compounds were prepared from the corresponding 2-[(2,5-dichloro-4-pyrimidinyl)amino]-6-fluorobenzamide Intermediate 28 and the corresponding aniline following a procedure substantially as described for the preparation of Example 1.

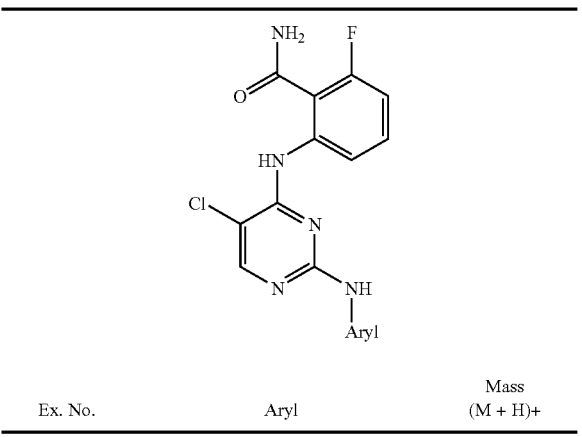

| Ex. No. | Aryl | Mass (M + H)+ |
|---|---|---|
| 117 | | 441 |
| 118 | | 471 |

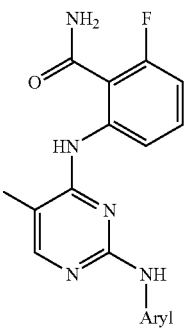

| Ex. No. | Aryl | Mass (M + H)+ |
|---|---|---|
| 119 | | 456 |

EXAMPLES 120-127

The following 2-{[5-chloro-2-(substituted phenylamino)-4-pyrimidinyl]amino}-6-fluoro-N-methylbenzamide compounds were prepared from the corresponding 2-[(2,5-dichloro-4-pyrimidinyl)amino]-6-fluoro-N-methylbenzamide Intermediate 30 and the corresponding aniline following a procedure substantially as described for the preparation of Example 1.

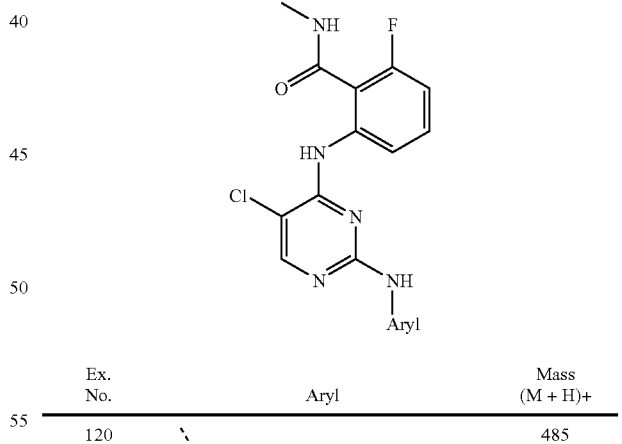

| Ex. No. | Aryl | Mass (M + H)+ |
|---|---|---|
| 120 | | 485 |
| 121 | | 470 |

-continued

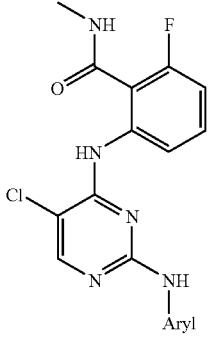

| Ex. No. | Aryl | Mass (M + H)+ |
|---|---|---|
| 122 | 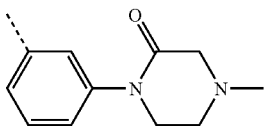 | 484 |
| 123 | 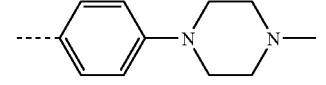 | 470 |
| 124 | 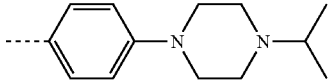 | 499 |
| 125 | 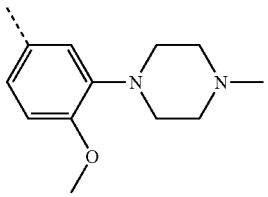 | 500 |
| 126 | 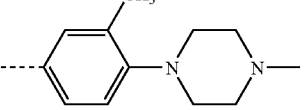 | 484 |
| 127 | 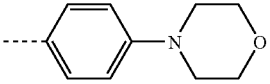 | 457 |

EXAMPLES 128-134

The following 2-{[5-chloro-2-(substituted phenylamino)-4-pyrimidinyl]amino}-6-fluoro-N-isopropylbenzamide compounds were prepared from the corresponding 2-[(2,5-dichloro-4-pyrimidinyl)amino]-6-fluoro-N-isopropylbenzamide Intermediate 31 and the corresponding aniline following a procedure substantially as described for the preparation of Example 1.

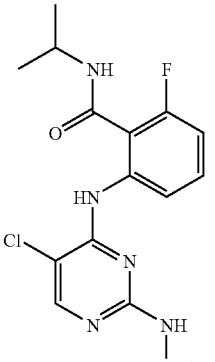

| Ex. No. | Aryl | Mass (M + H)+ |
|---|---|---|
| 128 | 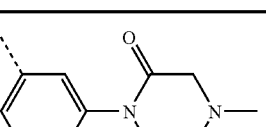 | 512 |
| 129 | 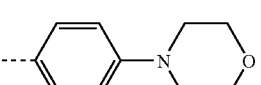 | 485 |
| 130 | 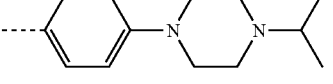 | 527 |
| 131 | 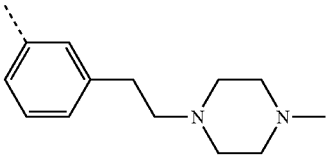 | 526 |
| 132 | 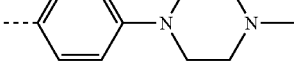 | 498 |
| 133 | 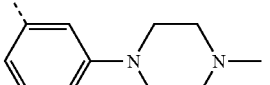 | 498 |
| 134 | 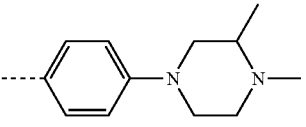 | 512 |

INTERMEDIATE 32

2-Amino-5-fluorobenzamide

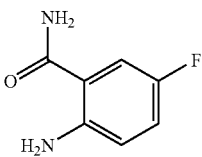

A round-bottomed flask was charged with 5-fluoroanthranilic acid (3 g, 19.34 mmol) in tetrahydrofuran (64.5 mL) and a 20% solution of phosgene (11.2 mL, 21.3 mmol) in toluene was added dropwise at room temperature. The mixture was stirred for 18 hr at room temperature, then cooled to 0° C., at which time concentrated ammonium hydroxide (27.9 mL, 193 mmol) was added cautiously. The mixture was then allowed to warm to room temperature and then stirred for 1 hr. The organic phase was diluted with EtOAc, washed with aqueous dipotassium hydrogen phosphate and brine, then dried over sodium sulfate and concentrated to give a white solid (2.46 g, 82% yield). MS: $M(C_7H_7FN_2O)=154.14$, $(M+H-NH_3)^+=138$.

INTERMEDIATE 33

2-Amino-4-fluoro-N-methylbenzamide

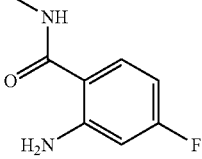

A microwave vial was charged with 7-fluoro-2H-3,1-benzoxazine-2,4(1H)-dione (750 mg, 4.14 mmol) and methyl amine 40% aqueous solution (19.8 mL, 22.8 mmol, 5.5 eq). The reaction was stirred and heated in the microwave for 6 min at 110° C. The aqueous solution was extracted with methylene chloride (3×). Organic layers were combined and washed with 5% $NaHCO_3$ solution and brine, dried over sodium sulfate, then concentrated to give a pale yellow oil that was used without further purification (434 mg, 62% yield). MS: $M(C_8H_9FN_2O)=168.17$, $(M+H)^+=169$ and $(M+H-NHMe)^+=138$.

INTERMEDIATE 34

2-[(2,5-Dichloro-4-pyrimidinyl)amino]-5-fluorobenzamide

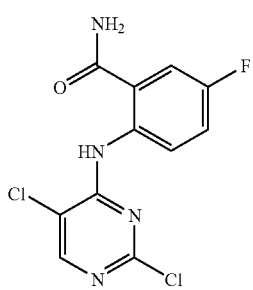

A vessel was charged with 2,4,5-trichloropyrimidine (2.29 mL, 20 mmol), 2-amino-5-difluorobenzamide (1.54 g, 10 mmol), di-isopropyl-ethylamine (7.43 mL, 425 mmol) and 33 mL isopropanol. The vessel was sealed and heated with stirring at 95° C. for 36 h. A white solid appeared in the reaction mixture. The reaction was cooled to room temperature, and the solid was filtered off and washed with isopropanol followed by $Et_2O$. After drying, the white solid (2.36 g, 78% yield) was identified as 2-[(2,5-dichloro-4-pyrimidinyl)amino]-5-fluorobenzamide. MS: $M(C_{11}H_7Cl_2FN_4O)=301.10$, $(M+H)^+=301, 303, 305$.

Intermediates 35-37

The following 2-[(2,5-dichloro-4-pyrimidinyl)amino]-fluorobenzamide compounds were prepared from the corresponding 2-aminofluorobenzamide and 2,4,5-trichloropyrimidine following a procedure substantially as described for the preparation of Example 1.

| Int. No. | Structure | Mass (M + H)+ |
|---|---|---|
| 35 | 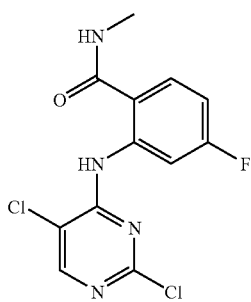 | 301 |
| 36 | 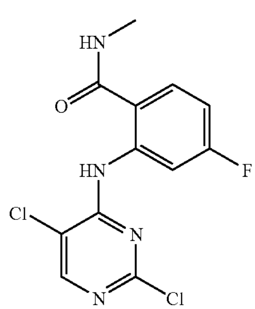 | 315, 317 |

-continued

| Int. No. | Structure | Mass (M + H)+ |
|---|---|---|
| 37 | (5-bromo-2-((2,5-dichloropyrimidin-4-yl)amino)benzamide structure) | 360, 362, 364 |

EXAMPLES 135-137

The following 2-{[5-chloro-2-(arylamino)-4-pyrimidinyl]amino}-4-fluoro-N-methylbenzamide compounds were prepared from the corresponding 2-[(2,5-dichloro-4-pyrimidinyl)amino]-4-fluoro-N-methylbenzamide Intermediate 36 and the corresponding aniline following a procedure substantially as described for the preparation of Example 1.

| Ex. No. | Aryl | Mass (M + H)+ |
|---|---|---|
| 135 | 2-methyl-4-(4-methylpiperazin-1-yl)phenyl | 484, 485, 486, 487 |
| 136 | 3-(morpholinomethyl)phenyl (via CH2) | 465, 487 |
| 137 | 3-(4-methyl-3-oxopiperazin-1-yl)phenyl | 484, 486 |

EXAMPLES 138-140

The following 2-{[5-chloro-2-(arylamino)-4-pyrimidinyl]amino}-5-fluorobenzamide compounds were prepared from the corresponding 2-[(2,5-dichloro-4-pyrimidinyl)amino]-5-fluorobenzamide Intermediate 34 and the corresponding aniline following a procedure substantially as described for Example 1.

| Ex. No. | Aryl | Mass (M + H)+ |
|---|---|---|
| 138 | 3-(pyrrolidin-1-ylmethyl)phenyl | 441, 443 |
| 139 | 3-(2-morpholinoethyl)phenyl | 471, 473 |
| 140 | 4-(4-isopropylpiperazin-1-yl)phenyl | 484, 486 |

EXAMPLE 141

5-Bromo-2-[(5-chloro-2-{[3-(1-pyrrolidinylmethyl)phenyl]amino}-4-pyrimidinyl)amino]benzamide

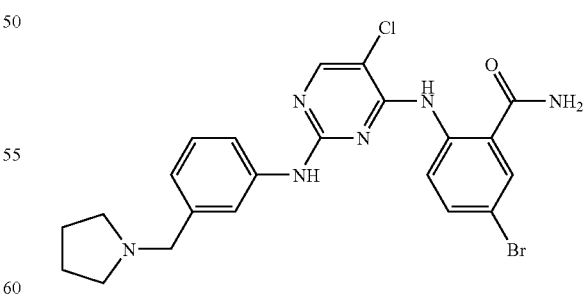

5-Bromo-2-[(5-chloro-2-{[3-(1-pyrrolidinylmethyl)phenyl]amino}-4-pyrimidinyl)amino]benzamide was prepared by contacting 5-bromo-2-[(2,5-dichloro-4-pyrimidinyl)amino]benzamide (Intermediate 37) with 3-pyrrolidinylmethylaniline following a procedure substantially as described for the preparation of Example 1. Mass (M+H)+501, 503, 505

EXAMPLES 142-144

The following 2-{[5-chloro-2-(arylamino)-4-pyrimidinyl]amino}-4-fluorobenzamide compounds were prepared from the corresponding 2-[(2,5-dichloro-4-pyrimidinyl)amino]-4-fluorobenzamide (Intermediate 35) and the corresponding aniline following a procedure substantially as described for the preparation of Example 1.

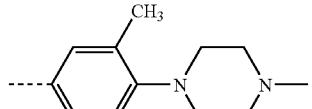

| Ex. No. | Aryl | Mass (M + H)+ |
|---|---|---|
| 142 | 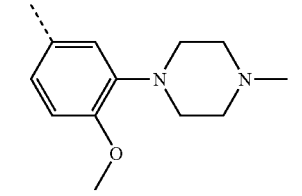 | 470, 472 |
| 143 | 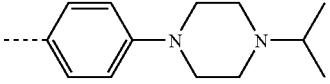 | 471, 473 |
| 144 | 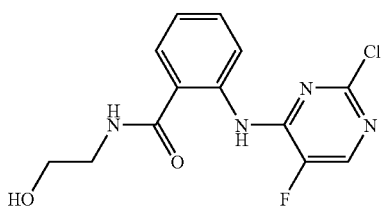 | 484, 486 |

INTERMEDIATE 38

2-[(2-Chloro-5-fluoro-4-pyrimidinyl)amino]-N-(2-hydroxyethyl)benzamide

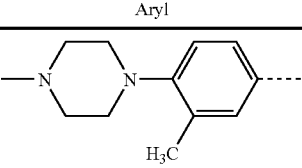

A round-bottomed flask was charged with 2,4-dichloro-5-fluoropyrimidine (3.0 g, 0.018 mol), 2-amino-N-(2-hydroxyethyl)benzamide (3.3 g, 0.018 mol), di-isopropyl-ethylamine (3.7 mL, 0.021 mol) and 50 mL isopropanol. The flask was fitted with a reflux condenser and the mixture was heated to reflux and stirred for 18 h. A white solid appeared in the reaction mixture. The reaction was cooled to room temperature, and the solid was filtered off and washed with isopropanol and ether. After drying, the white solid (5.09 g, 88% yield) was identified as 2-[(2-chloro-5-fluoro-4-pyrimidinyl)amino]-N-(2-hydroxyethyl)benzamide.

EXAMPLE 145

2-{[5-Fluoro-2-({3-[2-(4-morpholinyl)ethyl]phenyl}amino)-4-pyrimidinyl]amino}-N-(2-hydroxyethyl)benzamide

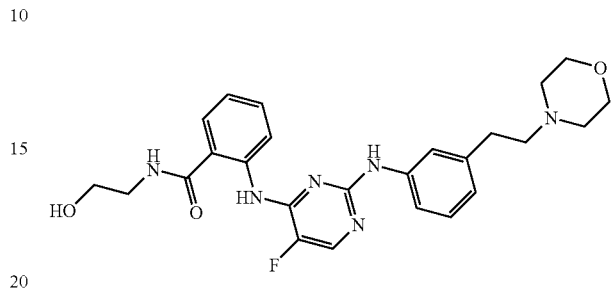

2-[(2-Chloro-5-fluoro-4-pyrimidinyl)amino]-N-(2-hydroxyethyl)benzamide (500 mg, 1.61 mmol) and 3-(morpholinoethyl)aniline (352 mg, 1.61 mmol) were combined in a tube with 30 mL isopropanol and 12N HCl (134 µL, 1.60 mmol). The vessel was sealed and heated with stirring at 90° C. for 18 h. The reaction was cooled to room temperature and the solid was filtered off and washed with isopropanol and ether to give 550 mg (71% yield) of a white solid as the HCl salt, LC/MS (M+H)+480, 481.

EXAMPLES 146-153

The following 2-{[5-fluoro-2-(arylamino)-4-pyrimidinyl]amino}-N-(2-hydroxyethyl)benzamide compounds were prepared from the corresponding 2-[(2-chloro-5-fluoro-4-pyrimidinyl)amino]-N-(2-hydroxyethyl)benzamide (Intermediate 38) and the corresponding aniline following a procedure substantially as described for the preparation of Example 145.

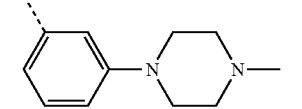

| Ex. No. | Aryl | Mass (M + H)+ |
|---|---|---|
| 146 |  | 479, 480 |
| 147 |  | 465, 466 |

-continued

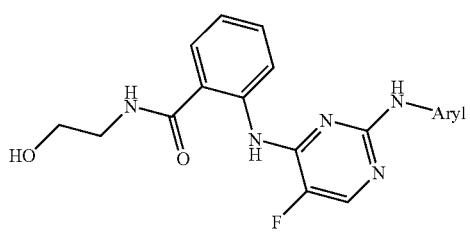

| Ex. No. | Aryl | Mass (M + H)+ |
|---|---|---|
| 148 | (4-isopropyl-piperazinyl)phenyl | 494, 495 |
| 149 | 4-(4-methyl-1-piperazinyl)phenyl | 466, 467 |
| 150 | 2-methoxy-5-(4-methyl-1-piperazinyl)phenyl | 496, 497 |
| 151 | 4-[2-(4-methyl-1-piperazinyl)ethyl]phenyl | 494, 495 |
| 152 | 3-(4-methyl-2-oxo-1-piperazinyl)phenyl | 480, 481 |
| 153 | 3-methyl-5-(4-methyl-1-piperazinyl)phenyl | 480, 481 |

INTERMEDIATE 39

Ethyl 2-[(2,5-dichloro-4-pyrimidinyl)amino]benzoate

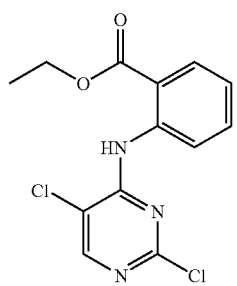

A round-bottomed flask was charged with 2,4,5-trichloro-pyrimidine (5 mL, 43.6 mmol), ethyl 2-aminobenzoate (7.6 g, 46.0 mmol), di-isopropyl-ethylamine (8.3 mL, 48.0 mmol) and ethanol (60 mL). The flask was fitted with a reflux condenser and the reaction was heated to reflux and stirred for 18 h. A white solid appeared in the reaction mixture. The reaction was cooled to room temperature, and the solid was filtered off and washed with ethanol (100 mL), ethanol/hexane (1:1, 200 mL) and hexane (200 mL) to afford the product (10.2 g, 32.7 mmol, 75% yield) as a white solid. MS: $M(C_{13}H_{11}Cl_2N_3O_2)$=312.15, $(M+H)^+$=312.0 and 314.0.

INTERMEDIATE 40

Ethyl 2-[(5-chloro-2-{[3-(4-methyl-1-piperazinyl)phenyl]amino}-4-pyrimidinyl)amino]benzoate

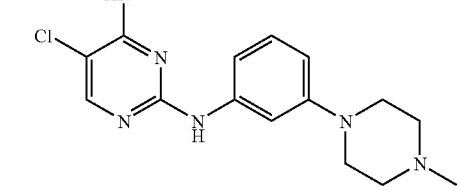

Ethyl 2-[(2,5-dichloro-4-pyrimidinyl)amino]benzoate (10.2 g, 32.8 mmol) and 3-(4-methyl-1-piperazinyl)aniline (6.6 g, 34.4 mmol) were combined in a vessel with ethanol (200 mL) and concentrated HCl (3.2 mL, 38.4 mmol, 12N). The vessel was sealed and heated with stirring at 95° C. for 24 h. The reaction was cooled to room temperature and poured onto water (1.3 L). The aqueous layer was extracted with ethyl acetate (2×250 mL) and neutralized to pH 7 by the slow addition of 6N NaOH. The precipitated solid was filtered off and washed with water and ethyl ether to afford the product (15.0 g, 98% yield) as a tan solid. MS: M($C_{24}H_{27}ClN_6O_2$)= 466.97, (M+H)+=467.2 and 469.2.

INTERMEDIATE 41

Ethyl 2-{[5-chloro-2-({3-[2-(4-morpholinyl)ethyl]phenyl}amino)-4-pyrimidinyl]amino}benzoate

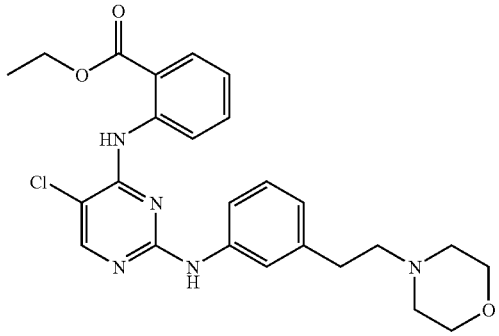

Ethyl 2-[(2,5-dichloro-4-pyrimidinyl)amino]benzoate (8.9 g, 28.5 mmol) and 3-[2-(4-morpholinyl)ethyl]aniline (6.2 g, 30.0 mmol) were combined in a vessel with ethanol (200 mL) and concentrated HCl (2.75 mL, 33.0 mmol, 12N). The vessel was sealed and heated with stirring at 95° C. for 24 h. The reaction was cooled to room temperature and filtered. The solid was washed with ethanol followed by hexanes, and then dried to afford 8 g of product which contained residual (~10%) ethyl 2-[(2,5-dichloro-4-pyrimidinyl)amino]benzoate. A portion of the crude product (6 g) was partitioned between ethyl acetate (100 mL) and 1N HCl (150 mL). The organic layer was extracted with 1N HCl, and the combined aqueous layers were cooled in an ice bath and basified to pH 9-10 by dropwise addition of 50% NaOH, keeping the temperature below 10° C. The precipitated solid was collected, washed with water and dried in vacuo over $P_2O_5$ to provide ethyl 2-{[5-chloro-2-({3-[2-(4-morpholinyl)ethyl]phenyl}amino)-4-pyrimidinyl]amino}benzoate as an off-white solid (4.7 g). MS: M($C_{25}H_{28}ClN_5O_3$)=481.98, (M+H)+= 482.2 and 484.2.

EXAMPLE 154

2-[(5-Chloro-2-{[3-(4-methyl-1-piperazinyl)phenyl]amino}-4-pyrimidinyl)amino]-N-[(1S)-2-hydroxy-1-methylethyl]benzamide

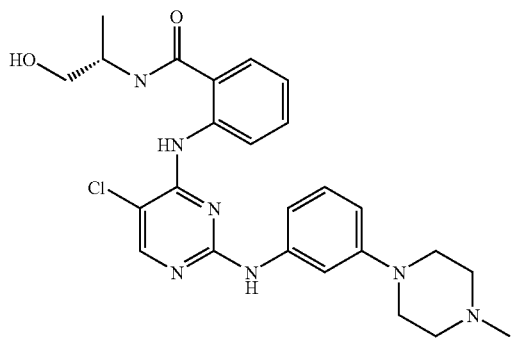

Ethyl 2-[(5-chloro-2-{[3-(4-methyl-1-piperazinyl)phenyl]amino}-4-pyrimidinyl)amino]benzoate (150 mg, 0.32 mmol) and (2S)-2-amino-1-propanol (0.5 mL) were combined in a vessel, which was sealed and heated with stirring at 95° C. for 18 h. The reaction was cooled to room temperature and the solid was filtered off and washed with ethanol/water (1:1 ratio) and ethyl ether to afford the product (82 mg, 52% yield) as a white solid. MS: M($C_{25}H_{30}ClN_7O_2$)=496.01, (M+H)+= 496.2 and 498.2.

EXAMPLES 155-161

The following 2-[(5-chloro-2-{[3-(4-methyl-1-piperazinyl)phenyl]amino}-4-pyrimidinyl)amino]-N-[substituted] benzamide compounds were prepared from ethyl 2-[(5-chloro-2-{[3-(4-methyl-1-piperazinyl)phenyl]amino}-4-pyrimidinyl)amino]benzoate and the corresponding aminoalcohol following a procedure substantially as described for the preparation of Example 154.

| Ex. No. | R | Mass (M + H)+ |
|---|---|---|
| 155 | HO-CH2-CH(CH3)-NH- | 496, 498 |
| 156 | HO-CH2-CH(CH(CH3)2)-NH- | 524, 526 |
| 157 | HO-CH2-CH(CH(CH3)2)-NH- | |
| 158 | HO-CH2-CH(CH2CH3)-NH- | 510, 512 |
| 159 | HO-CH2-CH(CH2CH3)-NH- | 510, 512 |

-continued

| Ex. No. | R | Mass (M + H)+ |
|---|---|---|
| 160 | (S)-HO-CH(CH₃)-CH₂-NH- | 496, 498 |
| 161 | (R)-HO-CH(CH₃)-CH₂-NH- | 496, 498 |

EXAMPLES 162-176

The following substituted 2-{[5-chloro-2-({3-[2-(4-morpholinyl)ethyl]phenyl}amino)-4-pyrimidinyl]amino}benzamide compounds were prepared from ethyl 2-{[5-chloro-2-({3-[2-(4-morpholinyl)ethyl]phenyl}amino)-4-pyrimidinyl]amino}benzoate (Intermediate 41) and the corresponding aminoalcohol following a procedure substantially as described for the preparation of Example 154.

| Ex. No. | R | Mass (M + H)+ |
|---|---|---|
| 162 | cyclobutyl-NH- | 507.2, 509.2 |
| 163 | (S)-HOCH₂-CH(CH₃)-NH- | 510.8, 512.8 |
| 164 | (R)-HOCH₂-CH(CH₃)-NH- | 510.8, 512.8 |
| 165 | (CH₃)₂CH-CH₂-CH₂-NH- | 522.8, 524.8 |
| 166 | (tetrahydrofuran-2-yl)-CH₂-NH- | 537.2, 539.2 |
| 167 | (S)-3-hydroxypyrrolidin-1-yl | 522.8, 524.8 |
| 168 | 2-(hydroxymethyl)pyrrolidin-1-yl | 536.8, 538.8 |
| 169 | (2S,3S)-3-methyl-1-hydroxypentan-2-yl-NH- | 552.8, 554.8 |
| 170 | (S)-3,3-dimethyl-1-hydroxybutan-2-yl-NH- | 552.8, 554.8 |
| 171 | (S)-4-methyl-1-hydroxypentan-2-yl-NH- | 552.8, 554.8 |

-continued

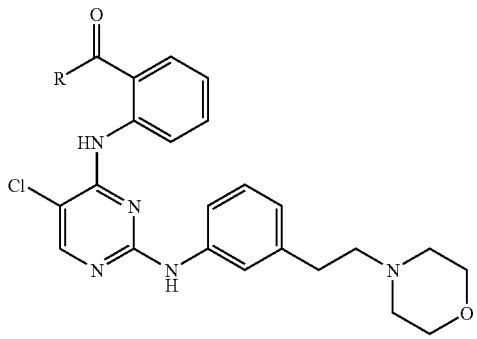

| Ex. No. | R | Mass (M + H)+ |
|---|---|---|
| 172 | 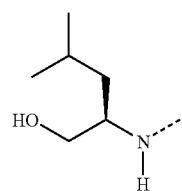 | 552.8, 554.8 |
| 173 | 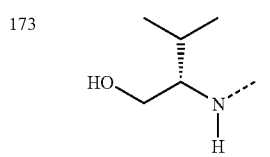 | 538.8, 540.8 |
| 174 | 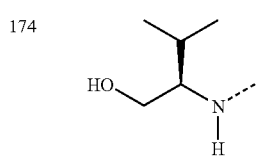 | 538.8, 540.8 |
| 175 | 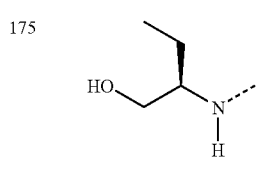 | 536.8, 538.8 |
| 176 | 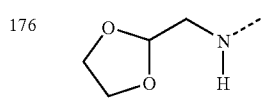 | 539.2, 540.2, 541.2, 542.2 |

INTERMEDIATE 42

Ethyl 2-[(2-chloro-5-fluoro-4-pyrimidinyl)amino]benzoate

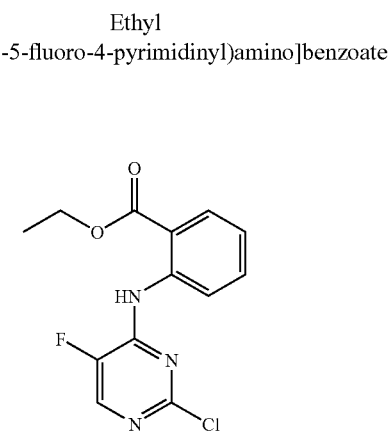

A round-bottomed flask was charged with 2,4-dichloro-5-fluoropyrimidine (2.5 g, 15 mmol), ethyl 2-aminobenzoate (4.9 g, 30 mmol), N,N-diisopropylethylamine (5.2 mL, 3.9 g, 30 mmol) and isopropanol (50 mL). The flask was fitted with a reflux condenser and the mixture was heated to reflux and stirred for 18 h. After cooling the reaction mixture to room temperature a precipitate appeared. The solid was collected and washed sparingly with isopropanol then copiously with ethyl ether to afford the title compound as a white solid; yield, 1.8 g (41%). MS: $M(C_{13}H_{13}ClFN_3O_2)=295.70$ $(M+H)^+=296.0$ and 298.0.

INTERMEDIATE 43

Ethyl 2-[(5-fluoro-2-{[3-(4-methyl-1-piperazinyl)phenyl]amino}-4-pyrimidinyl)amino]benzoate

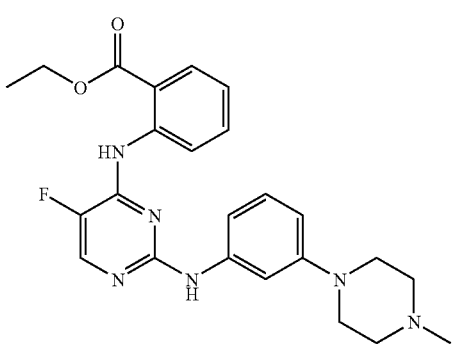

Ethyl 2-[(2-chloro-5-fluoro-4-pyrimidinyl)amino]benzoate (1.0 g, 3.4 mmol), 3-(4-methyl-1-piperazinyl)aniline (0.65 g, 3.4 mmol), ethanol (45 mL) and 6N HCl (1.5 mL, 8.8 mmol) were heated with stirring in a reaction vessel, which was sealed and heated at 95° C. for 24 h. The reaction mixture was cooled to room temperature, poured into water, extracted with ethyl acetate and neutralized to pH 7 by the slow addition of 6N NaOH. The resulting precipitate was collected on a sintered glass funnel and washed with water and ethyl ether to afford the title compound as a tan solid; yield 1.0 g (65%). MS: $M(C_{24}H_{27}FN_6O_2)=450.52$ $(M+H)^+=451.2$.

EXAMPLE 177

(3R)-1-({2-[(5-Fluoro-2-{[3-(4-methyl-1-piperazinyl)phenyl]amino}-4-pyrimidinyl)amino]phenyl}carbonyl)-3-pyrrolidinol

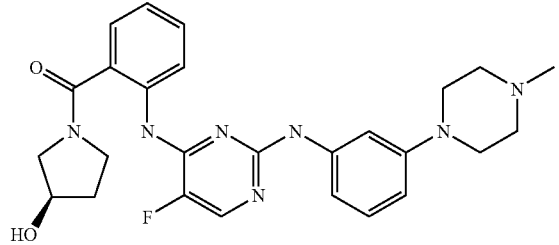

Ethyl 2-{[5-fluoro-2-({3-[2-(4-morpholinyl)ethyl]phenyl}amino)-4-pyrimidinyl]amino}benzoate (0.25 g, 0.55 mmol) and (R)-(+)-3-pyrrolidinol mL, (1 mL) were combined in a tube, which was sealed and heated with stirring at 125° C. for 18 h. The reaction was cooled to room temperature and ethyl acetate was added to the residue to afford a light gray solid; yield 0.15 g (55%). Recrystallization from MeOH/H2O afforded the title compound as a tan solid (25 mg.). MS: $M(C_{26}H_{30F}N_7O_2)=491.57$ $(M+H)^+=492.2$.

INTERMEDIATE 44

Ethyl 2-[(2-chloro-5-methyl-4-pyrimidinyl)amino]benzoate

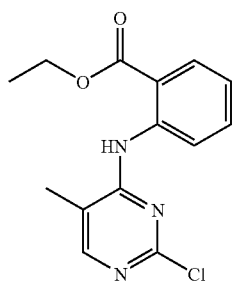

2,4-Dichloro-5-methylpyrimidine (28.1 g, 4172 mmol), ethyl 2-aminobenzoate (26.7 mL, 181 mmol), diisopropylethylamine (33 mL, 190 mmol) and ethanol (200 mL) were mixed together then equally divided and placed in two 350 mL pressure vessels. They were then capped and heated to 130° C. for three days. Upon cooling to room temperature, the precipitated product was collected and washed with ethanol followed by hexanes and then dried to give 4.5 g (9%) of ethyl 2-[(2-chloro-5-methyl-4-pyrimidinyl)amino]benzoate as an off-white solid. MS: $M(C_{14}H_{14}ClN_3O_2)=291.7$, $(M+H)^+=292.2$ and 294.2.

INTERMEDIATE 45

Ethyl 2-{[5-methyl-2-({3-[2-(4-morpholinyl)ethyl]phenyl}amino)-4-pyrimidinyl]amino}benzoate

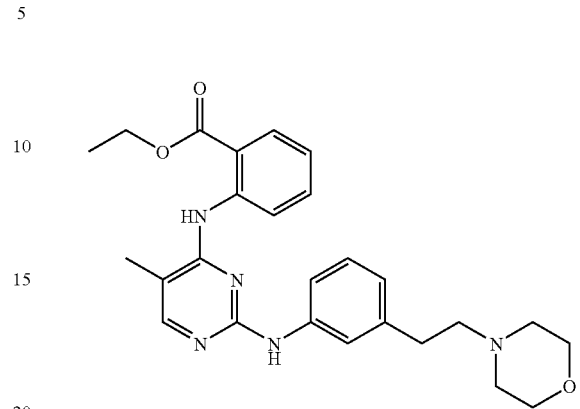

Ethyl 2-[(2-chloro-4-pyrimidinyl-5-methyl)amino]benzoate (200 mg, 0.69 mmol) and 3-[2-(4-morpholinyl)ethyl]aniline (141 mg, 0.69 mmol) were combined in a vessel with isopropanol (5 mL) and 6N HCl (0.2 mL, 1.2 mmol). The vessel was sealed and heated with stirring at 90° C. for 18 h. The reaction was cooled to room temperature and evaporated. The residue was partitioned between ethyl acetate (10 ML) and sodium bicarbonate (10 mL). The organic layer was washed with brine, dried over magnesium sulfate, filtered and evaporated to provide the titled compound as a light yellow solid (300 mg). MS: $M(C_{26}H_{31}N_5O_3)=461.56$, $(M+H)^+=462.2$.

EXAMPLE 178

(3R)-1-[(2-{[5-Methyl-2-({3-[2-(4-morpholinyl)ethyl]phenyl}amino)-4-pyrimidinyl]amino}phenyl)carbonyl]-3-pyrrolidinol

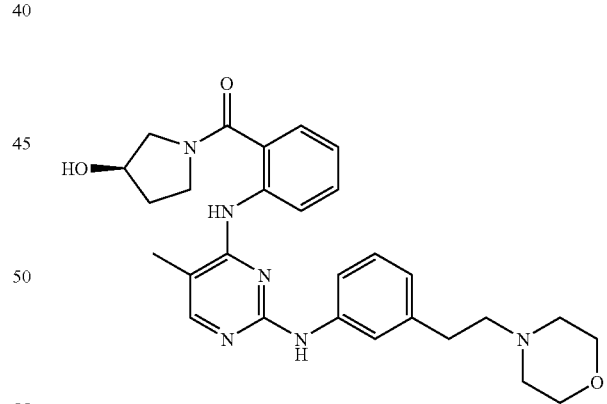

Ethyl 2-{[5-methyl-2-({3-[2-(4-morpholinyl)ethyl]phenyl}amino)-4-pyrimidinyl]amino}benzoate (135 mg, 0.29 mmol) and (R)-(+)-3-pyrrolidinol (0.23 mL, 0.29 mmol) were combined in a vessel with dioxane (1 mL). The vessel was sealed and heated with stirring at 125° C. for 18 h. The reaction was cooled to room temperature and evaporated. The residue was partitioned between ethyl acetate (10 mL) and water (10 mL). The organic layer was washed with brine, dried over magnesium sulfate, filtered and evaporated.

The residue was purified using normal phase HPLC eluting with a gradient of dichloromethane/methanol/ammonium hydroxide (90:10:0-90:10:1) affording the product as the free-base. Dissolution in MeOH followed by addition of concentrated HCl (excess) and evaporation gave the title compound as a dihydrochloride salt (tan solid, 65 mg, 45% yield). MS: M($C_{28}H_{34}N_6O_3$)=502.62, (M+H)$^+$=503.2.

EXAMPLE 179

(3S)-1-[(2-{[5-Methyl-2-({3-[2-(4-morpholinyl)ethyl]phenyl}amino)-4-pyrimidinyl]amino}phenyl)carbonyl]-3-pyrrolidinol

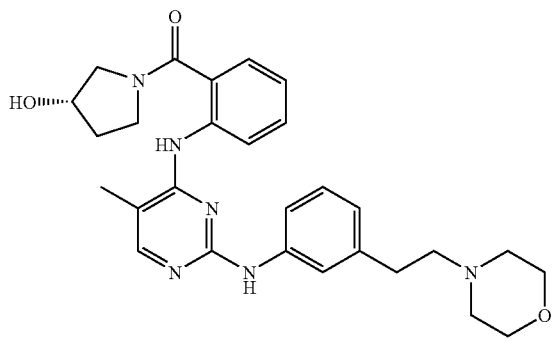

Ethyl 2-{[5-methyl-2-({3-[2-(4-morpholinyl)ethyl]phenyl}amino)-4-pyrimidinyl]amino}benzoate (135 mg, 0.29 mmol) and (S)-(+)-3-pyrrolidinol (0.23 mL, 0.29 mmol) were combined in a vessel with dioxane (1 mL). The vessel was sealed and heated with stirring at 125° C. for 18 h. The reaction was cooled to room temperature and evaporated. The residue was partitioned between ethyl acetate (10 mL) and water (10 mL). The organic layer was washed with brine, dried over magnesium sulfate, filtered and evaporated. The residue was purified using normal phase HPLC eluting with a gradient of dichloromethane/methanol/ammonium hydroxide (90:10:0-90:10:1) affording the product as the free-base. Dissolution in MeOH followed by addition of concentrated HCl (excess) and evaporation gave the title compound as a dihydrochloride salt (tan solid, 65 mg, 45% yield). MS: M($C_{28}H_{34}N_6O_3$)=502.62, (M+H)$^+$=503.2.

INTERMEDIATE 46

Ethyl 2-[(5-methyl-2-{[3-(4-methyl-1-piperazinyl)phenyl]amino}-4-pyrimidinyl)amino]benzoate

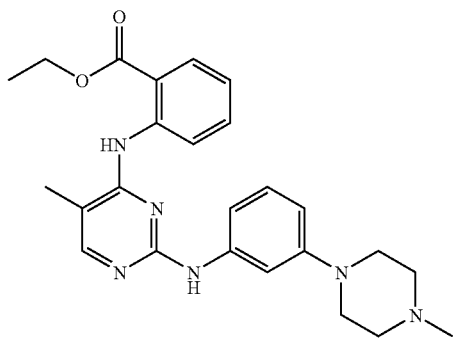

Ethyl 2-[(2-chloro-4-pyrimidinyl-5-methyl)amino]benzoate (200 mg, 0.69 mmol) and 3-(4-methyl-1-piperazinyl)aniline (132 mg, 0.69 mmol) were combined in a vessel with isopropanol (2 mL) and 6N HCl (0.2 mL, 1.2 mmol). The vessel was sealed and heated with stirring at 90° C. for 18 h. The reaction was cooled to room temperature and evaporated. The residue was partitioned between ethyl acetate (10 mL) and sodium bicarbonate (10 mL). The organic layer was washed with brine, dried over magnesium sulfate, filtered and evaporated to provide ethyl 2-{[5-methyl-2-({3-[2-(4-morpholinyl)ethyl]phenyl}amino)-4-pyrimidinyl]amino}benzoate as a light yellow solid (280 mg); yield MS: M($C_{25}H_{30}N_6O_2$)=446.55, (M+H)$^+$=447.2.

EXAMPLE 180

(3R)-1-({2-[(5-Methyl-2-{[3-(4-methyl-1-piperazinyl)phenyl]amino}-4-pyrimidinyl)amino]phenyl}carbonyl)-3-pyrrolidinol

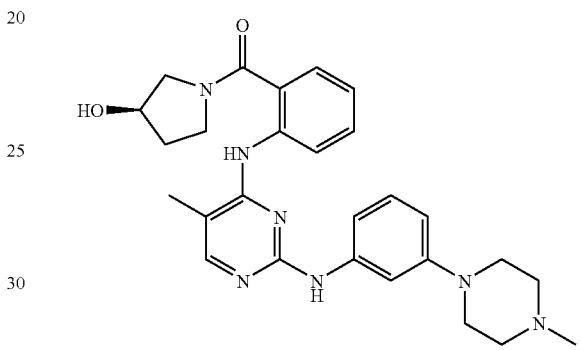

Ethyl 2-[(5-methyl-2-{[3-(4-methyl-1-piperazinyl)phenyl]amino}-4-pyrimidinyl)amino]benzoate (120 mg, 0.27 mmol) and (R)-(+)-3-pyrrolidinol (0.65 mL, used as solvent) were combined in a vessel, which was sealed and heated with stirring at 125° C. for 18 h. The reaction was cooled to room temperature and evaporated. The residue was partitioned between ethyl acetate (10 mL) and water (10 mL). The organic layer was washed with brine, dried over magnesium sulfate, filtered and evaporated. The residue was purified using normal phase HPLC eluting with a gradient of dichloromethane/methanol/ammonium hydroxide (90:10:0-90:10:1) affording the title compound as an off-white solid; yield 63 mg. (48%). (MS: M($C_{27}H_{33}N_7O_2$)=487.60, (M+H)$^+$=488.2.

EXAMPLE 181

(3S)-1-({2-[(5-methyl-2-{[3-(4-methyl-1-piperazinyl)phenyl]amino}-4-pyrimidinyl)amino]phenyl}carbonyl)-3-pyrrolidinol

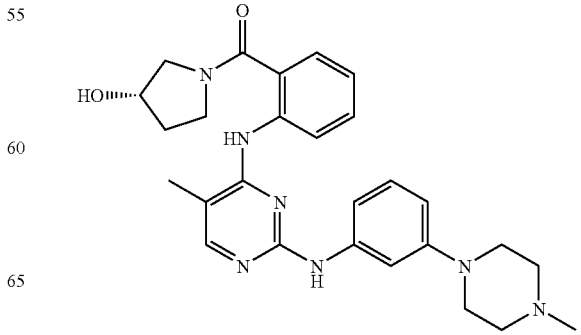

Ethyl 2-[(5-methyl-2-{[3-(4-methyl-1-piperazinyl)phenyl]amino}-4-pyrimidinyl)amino]benzoate (120 mg., 0.27 mmol) and (S)-(+)-3-pyrrolidinol (0.65 mL, used as solvent) were combined in a vessel, which was sealed and heated with stirring at 125° C. for 18 h. The reaction was cooled to room temperature and evaporated. The residue was partitioned between ethyl acetate (10 mL) and water (10 mL). The organic layer was washed with brine, dried over magnesium sulfate, filtered and evaporated. The residue was purified using normal phase HPLC eluting with a gradient of dichloromethane/methanol/ammonium hydroxide (90:10:0-90:10:1) affording the title compound as an off-white solid; yield 98 mg. (75%). MS: $M(C_{27}H_{33}N_7O_2)=487.60$, $(M+H)^+=488.2$.

EXAMPLES 182-183

The following 2-{[5-fluoro-2-(substituted phenylamino)-4-pyrimidinyl]amino}-N-(1-methylethyl)benzamide compounds were prepared from 2-[(2-chloro-5-fluoro-4-pyrimidinyl)amino]-N-(1-methylethyl)benzamide and the corresponding aniline following the procedure substantially as shown for Example 1. Product was isolated by filtration or by evaporation of the reaction mixture and purification by preparative HPLC.

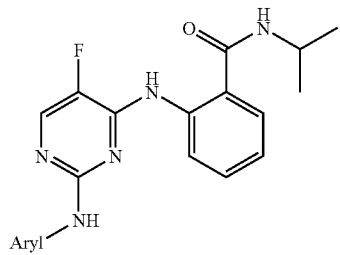

| Ex. No. | Aryl | Mass (M + H)+ |
|---|---|---|
| 182 | (4-position, piperazinyl-methyl-benzoyl) | 492, 493 |
| 183 | (3-position, piperazinyl-methyl-benzoyl) | 492, 493 |

EXAMPLE 184

5-Fluoro-$N^2$-{3-[2-(4-morpholinyl)ethyl]phenyl}-$N^4$-[2-(4-thiomorpholinylcarbonyl)phenyl]-2,4-pyrimidinediamine

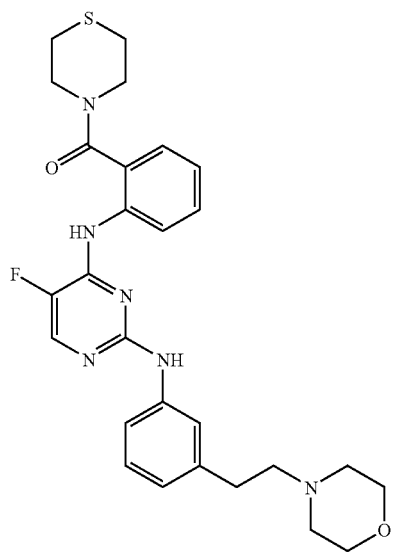

Ethyl 2-{[5-fluoro-2-({3-[2-(4-morpholinyl)ethyl]phenyl}amino)-4-pyrimidinyl]amino}benzoate (200 mg, 0.51 mmoles) and thiomorpholine (2 mL) were heated at 120° C. for 48 h. The reaction mixture was concentrated to dryness under vacuum and the title compound was purified by flash chromatography on silica gel (using ethyl acetate containing 0.1% triethylamine). MS: $M(C_{27}H_{31}FN_6O_2S)=522.2$, $(M+H)^+=523$.

EXAMPLE 185

$N^4$-{2-[(1,1-Dioxido-4-thiomorpholinyl)carbonyl]phenyl}-5-fluoro-$N^2$-{3-[2-(4-morpholinyl)ethyl]phenyl}-2,4-pyrimidinediamine

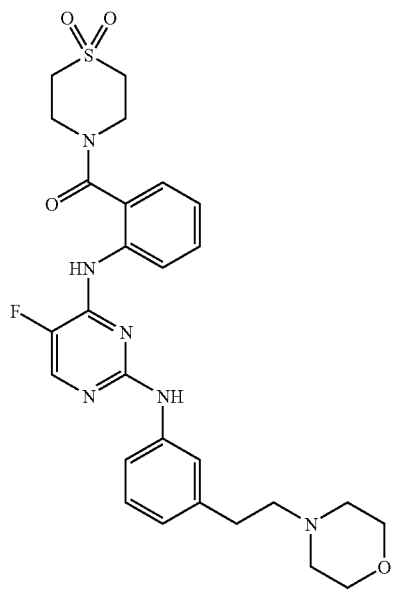

5-fluoro-$N^2$-{3-[2-(4-morpholinyl)ethyl]phenyl}-$N^4$-[2-(4-thiomorpholinylcarbonyl)phenyl]-2,4-pyrimidinediamine (100 mg, 0.19 mmoles) was dissolved in 5 mL of THF and 5 mL of methanol, and treated with a solution of OXONE® reagent (15 equivalents) in 5 mL water. The system was stirred for 48 h at room temperature, and then filtered and concentrated to dryness. The residue was immobilized onto silica gel and purified by flash chromatography on silica gel, using a gradient of 100% A to 90% A-10% B, where "A" is chloroform and "B" is 10:90:1 methanol-chloroform-concentrated aqueous ammonium hydroxyde). The title compound was isolated and characterized. MS: $M(C_{27}H_{31}FN_6O_4S)=554.2$, $(M+H)^+=555$.

EXAMPLE 186

2-{[5-Fluoro-2-({3-[2-(4-morpholinyl)ethyl]phenyl}amino)-4-pyrimidinyl]amino}-N-[2-(methylthio)ethyl]benzamide

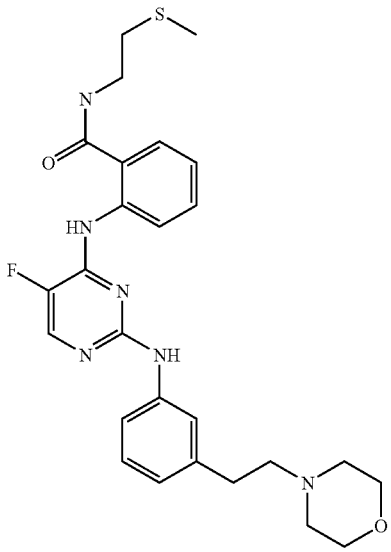

Ethyl 2-{[5-fluoro-2-({3-[2-(4-morpholinyl)ethyl]phenyl}amino)-4-pyrimidinyl]amino}benzoate (200 mg, 0.51 mmoles) and 2-(methylthio)ethylamine (2 mL) were heated at 120° C. for 48 h. The reaction mixture was concentrated to dryness under vacuum and the title compound was purified by flash chromatography on silica gel (ethyl acetate containing 0.1% triethylamine). MS: $M(C_{26}H_{31}FN_6O_2S)=510.2$, $(M+H)^+=511$.

EXAMPLES 187 and 188

2-{[5-fluoro-2-({3-[2-(4-morpholinyl)ethyl]phenyl}amino)-4-pyrimidinyl]amino}-N-[2-(methylsulfinyl)ethyl]benzamide

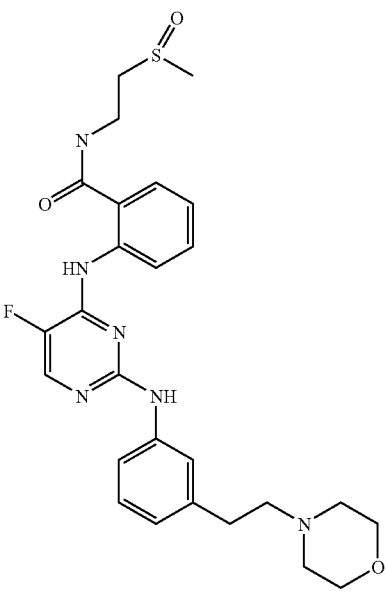

187 and

2-{[5-fluoro-2-({3-[2-(4-morpholinyl)ethyl]phenyl}amino)-4-pyrimidinyl]amino}-N-[2-(methylsulfonyl)ethyl]benzamide

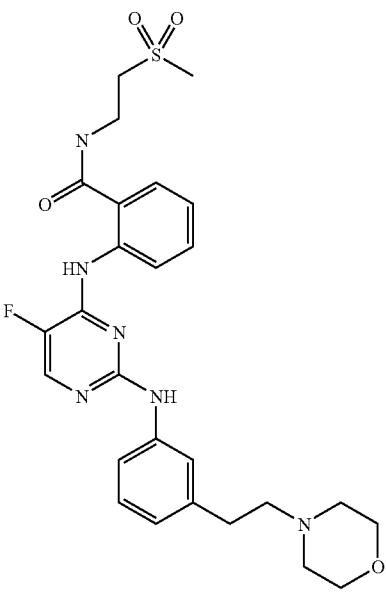

188

2-{[5-Fluoro-2-({3-[2-(4-morpholinyl)ethyl]phenyl}amino)-4-pyrimidinyl]amino}-N-[2-(methylthio)ethyl]benzamide (100 mg, 0.20 mmoles) was dissolved in 5 mL of THF and 5 mL of methanol, and treated with a solution of OXONE® reagent (a registered trademark of DuPont, 15 equivalents) in 5 mL water. The system was stirred for 48 h at room temperature, and then filtered and concentrated to dryness. The residue was immobilized onto silica gel and purified by silica gel chromatography, using a gradient of 100% A to 90% A-10% B, where "A" is chloroform and "B" is 10:90:1 methanol-chloroform-concentrated aqueous ammonium hydroxide). The title compounds 2-{[5-fluoro-2-({3-[2-(4-morpholinyl)ethyl]phenyl}amino)-4-pyrimidinyl]amino}-N-[2-(methylsulfinyl)ethyl]benzamide (Example 187) and 2-{[5-fluoro-2-({3-[2-(4-morpholinyl)ethyl]phenyl}amino)-4-pyrimidinyl]amino}-N-[2-(methylsulfonyl)ethyl]benzamide were isolated and characterized.

Example 187 MS: $M(C_{26}H_{31}FN_6O_3S)=526.2$, $(M+H)^+=527$. Example 188 MS: $M(C_{26}H_{31}FN_6O_4S)=542.2$, $(M+H)^+=543$.

EXAMPLES 189-190

The following 2-{[5-bromo-2-(substituted phenylamino)-4-pyrimidinyl]amino}-N-(1-methylpropyl)benzamide compounds were prepared from 2-[(5-bromo-2-chloro-4-pyrimidinyl)amino]-N-(1-methylpropyl)benzamide and the corresponding aniline following a procedure substantially as described for the preparation of Example 1. Product was isolated by filtration or by evaporation of the reaction mixture and purified by preparative HPLC.

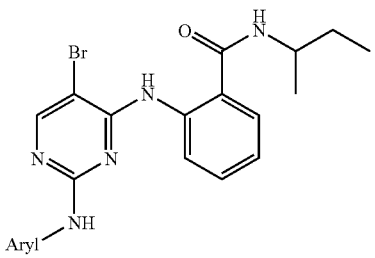

| Ex. No. | Aryl | Mass (M + H)+ |
|---|---|---|
| 189 | 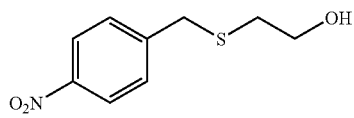 | 553, 555 |
| 190 | 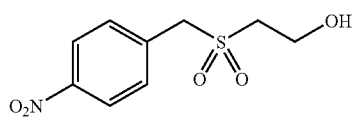 | 521, 523 |

INTERMEDIATE 147

2-{[(4-Nitrophenyl)methyl]thio}ethanol

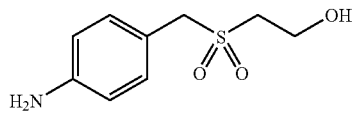

β-Mercaptoethanol (3.3 mL, 47.2 mmol) was added to a suspension of 4-nitrobenzyl bromide (10.0 g, 46.3 mmol), $K_2CO_3$ (16.1 g, 116.5 mmol), KI (154 mg, 0.9 mmol), and 18-crown-6 (258 mg, 1.0 mmol) in acetone (105 mL). The mixture was refluxed under $N_2$ for 1.5 h, cooled to room temperature, filtered through a pad of celite, and concentrated in vacuo. The filtrate was poured into water (100 mL) and extracted with $Et_2O$ (2×100 mL). The extracts were washed with brine (150 mL), dried over $Na_2SO_4$, filtered, and concentrated in vacuo to give an orange oil (11.78 g), which was used in the following step without purification. MS: $M(C_9H_{11}NO_3S)=213.26$, $(M-OH)^+=196.0$.

INTERMEDIATE 148

2-{[(4-Nitrophenyl)methyl]sulfonyl}ethanol

A solution of 2-{[(4-nitrophenyl)methyl]thio}ethanol (Intermediate 147, 11.78 g, 46.3 mmol theoretical) in $CH_2Cl_2$ (200 mL) was added to vessel containing a solution of m-chlorobenzoic acid (49.2 g, 213.8 mmol) in $CH_2Cl_2$ (500 mL). The mixture was stirred at room temperature for 1.5 h, then transferred to a separatory funnel and washed successively with sat. aq. $Na_2SO_3$ (2×500 mL), sat. aq. $NaHCO_3$ (2×500 mL), and water (1×400 mL). The organic phase was then dried over $Na_2SO_4$, filtered, and concentrated in vacuo to give a white solid (7.77 g) which was used in the following step without purification. MS: $M(C_9H_{11}NO_5S)=245.25$, $(M+Na)^+=268.0$.

INTERMEDIATE 149

2-{[(4-Aminophenyl)methyl]sulfonyl}ethanol

A suspension of 2-{[(4-Nitrophenyl)methyl]sulfonyl}ethanol (Intermediate 148, 7.64 g, 46.3 mmol theoretical) and 10 wt % Pd/C (788 mg) in MeOH was stirred under an atmosphere of $H_2$ at room temperature for 2 h, then filtered through a pad of celite. The filtrate was concentrated in vacuo, and the orange residue was recrystallized from MeOH/Et₂O to give the desired product as light yellow crystals (3.65 g, 17.0 mmol, 37% over 3 steps). MS: M(C₉H₁₃NO₃S)=215.27, (M+H)⁺=216.0.

INTERMEDIATE 150

2-({5-Fluoro-2-[(4-{[(2-hydroxyethyl)sulfonyl]methyl}phenyl)amino]-4-pyrimidinyl}amino)-N-(1-methylethyl)benzamide

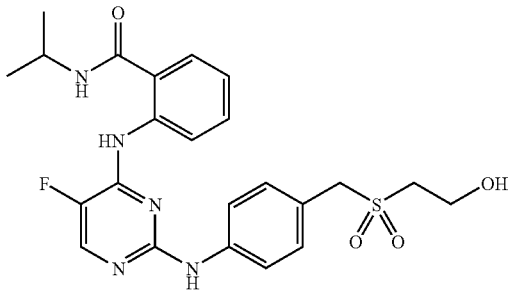

A mixture of 2-[(2-chloro-5-fluoro-4-pyrimidinyl)amino]-N-(1-methylethyl)benzamide (1.557 g, 5.04 mmol), Intermediate 149 (2-{[(4-aminophenyl)methyl]sulfonyl}ethanol, 1.085 g, 5.04 mmol), isopropanol (20 mL), and 6 M aq. HCl (0.1 mL) were stirred in a vessel, which was sealed and heated at 110° C. for 21 h. The mixture was allowed to cool, and a precipitate was collected by vacuum filtration to give the desired product as a tan solid (2.01 g, 4.12 mmol, 82%). MS: M(C₂₃H₂₆FN₅O₄S)=487.55, (M+H)⁺=488.

INTERMEDIATE 151

2-{[2-({4-[(Ethenylsulfonyl)methyl]phenyl}amino)-5-fluoro-4-pyrimidinyl]amino}-N-(1-methylethyl)benzamide

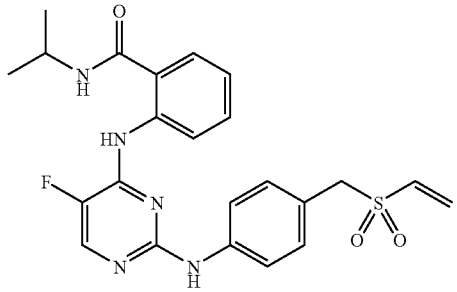

A suspension of Intermediate 150 (2-({5-fluoro-2-[(4-{[(2-hydroxyethyl)sulfonyl]methyl}phenyl)amino]-4-pyrimidinyl}amino)-N-(1-methylethyl)benzamide, 310 mg, 0.64 mmol) in CH₂Cl₂ (6 mL) under N₂ was cooled to 0° C. Triethylamine (0.35 mL, 2.51 mmol) was added, followed by dropwise addition of methanesulfonyl chloride (100 µL, 1.29 mmol). The mixture was stirred at 0° C. under N₂ for 45 min, then poured into water (20 mL), and extracted with 90/10 CH₂Cl₂/IPA (2×20 mL). The combined extracts were washed with sat. aq. NaHCO₃ (1×20 mL) and brine (1×20 mL), dried over Na₂SO₄, filtered, and concentrated in vacuo to give the desired product as a yellow solid (330 mg, ca. 80% purity) which was used in the following step without purification. MS: M(C₂₃H₂₄FN₅O₃S)=469.54, (M+H)⁺=470.2.

EXAMPLE 191

2-[(2-{[4-({[2-(Ethylamino)ethyl]sulfonyl}methyl)phenyl]amino}-5-fluoro-4-pyrimidinyl)amino]-N-(1-methylethyl)benzamide

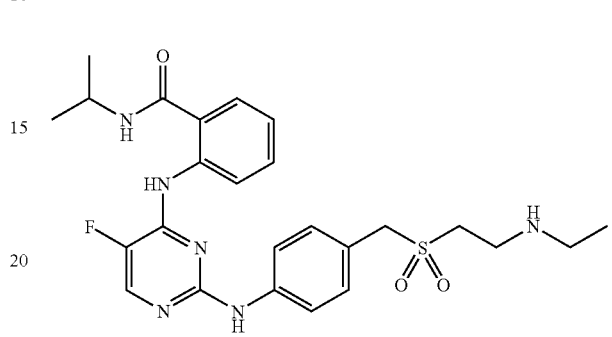

Ethyl amine (1.8 mL, 2.0 M in MeOH, 3.6 mmol) and Intermediate 151 (2-{[2-({4-[(ethenylsulfonyl)methyl]phenyl}amino)-5-fluoro-4-pyrimidinyl]amino}-N-(1-methylethyl)benzamide, 79 mg, 0.17 mmol), were combined in a vessel and stirred at room temperature for 1 h, then concentrated in vacuo to leave a residue The residue was taken up in MeOH with a few drops of TFA and purified by preparative reverse phase HPLC to give the TFA salt of the titled compound as a white solid (49 mg, 0.08 mmol, 46%). MS: M(C₂₅H₃₁FN₆O₃S)=514.62, (M+H)⁺=515.2.

EXAMPLES 192-197

The following 2-[(2-{[4-({[2-(alkylamino)ethyl]sulfonyl}methyl)phenyl]amino}-5-fluoro-4-pyrimidinyl)amino]-N-(1-methylethyl)benzamide analogs were prepared from Intermediate 151 (the vinyl sulfone) and the appropriate amine following the procedure substantially as shown for Example 191. The reactions were run in either MeOH or THF, and the products were purified by preparative reverse phase HPLC.

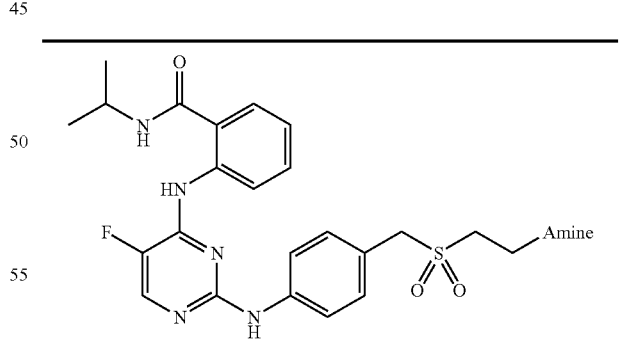

| Ex. No. | Amine | Mass (M + H)⁺ |
| --- | --- | --- |
| 192 | NEt₂ | 543 |
| 193 | NMe₂ | 515 |
| 194 | NH₂ | 487 |
| 195 | N-Methylpiperidinyl | 570 |
| 196 | morpholino | 557 |
| 197 | NHMe | 501 |

EXAMPLE 198

2-[(5-Fluoro-2-{[4-(4-piperidinyl)phenyl]amino}-4-pyrimidinyl)amino]-N-(1-methylethyl)benzamide

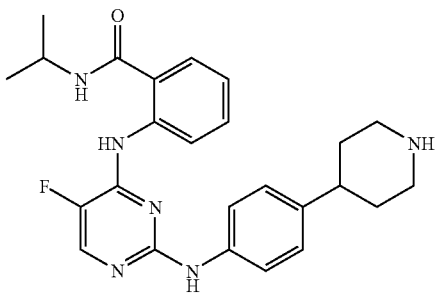

A mixture of 2-[(2-chloro-5-fluoro-4-pyrimidinyl)amino]-N-(1-methylethyl)benzamide (312 mg, 1.01 mmol), 4-(4-piperidinyl)aniline hydrochloride (213 mg, 1.00 mmol), and 6 M aq. HCl (0.09 mL, 0.54 mmol) in isopropanol (4 mL) was heated in a vessel, which was sealed and heated at 100° C. for 15 h. After cooling to room temperature the mixture was filtered, and the filtrate was concentrated in vacuo. The residue was taken up in 90/10/1 $CH_2Cl_2$/MeOH/$NH_4OH$, and again filtered and concentrated in vacuo, then purified by flash chromatography, eluting with a $CH_2Cl_2$ to 90/10/1 $CH_2Cl_2$/MeOH/$NH_4OH$ gradient. The product was dissolved in MeOH, to which was added 4 M HCl in dioxane, and the mixture was concentrated in vacuo to give the hydrochloride of Example 198 as a white solid (78 mg, 0.16 mmol, 16%). MS: $M(C_{25}H_{29}FN_6O)=448.54$, $(M+H)^+=449.2$.

EXAMPLES 199-201

The following 2-[(5-halo-2-{[4-(4-piperidinyl)phenyl]amino}-4-pyrimidinyl)amino]-N-(alkyl)benzamide compounds were prepared from the corresponding 2-[(2-chloro-5-halo-4-pyrimidinyl)amino]-N-(alkyl)benzamide and 4-(4-piperidinyl)aniline hydrochloride following a procedure substantially as described for the preparation of Example 198. Purifications were performed either by flash chromatography eluting with a $CH_2Cl_2$ to 90/10/1 $CH_2Cl_2$/MeOH/$NH_4OH$ gradient or by reverse phase HPLC.

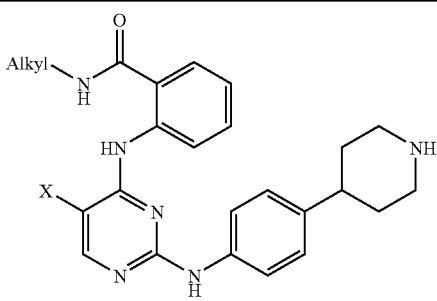

| Ex. No. | Alkyl | X | Mass (M + H)+ |
|---|---|---|---|
| 199 | i-Pr | F | 449 |
| 200 | i-Pr | Me | 445 |
| 201 | HO(CH$_2$)$_2$ | F | 451 |

EXAMPLE 202

Ethyl 4-({5-fluoro-4-[(2-{[(1 methylethyl)amino]carbonyl}phenyl)amino]-2pyrimidinyl}amino)benzoate

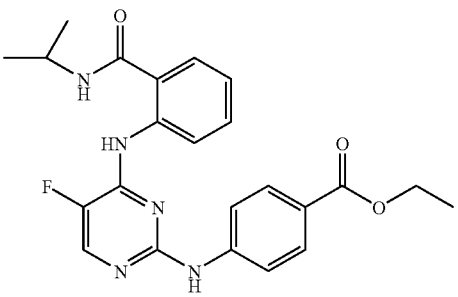

To the solution of 2-[(2-chloro-5-fluoro-4-pyrimidinyl)amino]-N-(1-methylethyl)benzamide (1.0 g, 3.25 mmol) in isopropanol (30 mL) was added ethyl 4-aminobenzoate (0.59 g, 3.57 mmol, 1.1 eq) followed 0.2 mL of 12N HCl. The reaction mixture was sealed in vessel and heated in a 95° C. oil bath for 16 h. The reaction was cooled to room temperature then white solid was precipitated. The white solid was collected by filtration and washed with cooled isopropyl alcohol (3×5 mL) to give the titled compound (1.1 g, 77% yield). MS: $M(C_{23}H_{23}FN_5O_3)=437.47$, $(M+H)^+=438$

EXAMPLE 203

2-[(5-Fluoro-2-{[4-(hydroxymethyl)phenyl]amino}-4-pyrimidinyl)amino]-N-(1-methylethyl)benzamide

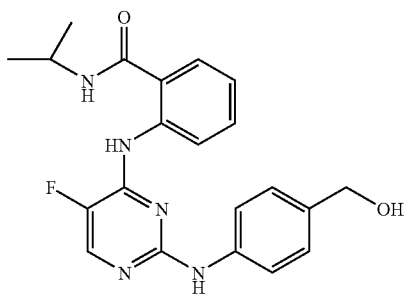

To a solution of ethyl 4-({5-fluoro-4-[(2-{[(1methylethyl)amino]carbonyl}phenyl)amino]-2-pyrimidinyl}amino)benzoate (1.47 g, 3.36 mmol) in THF (80 mL) was slowly added a solution of LiAlH$_4$ (1.0M solution, 3.0 eq) at 0° C. After the addition was complete, the reaction mixture was slowly warmed up to room temperature and stirred for 16 h. The reaction mixture was quenched with 15 mL of 1.0 M Rochelle's solution. The water phase was extracted by EtOAc (2×30 mL) and the combined organic phases were washed by brine (3×30 mL) then dried over Na$_2$SO$_4$. The solvent was evaporated to produce a solid, which was washed with hexane (3×30 mL), then dried in vacuo to give the desired product.

(1.15, 87% yield). MS: M($C_{21}H_{22}FN_5O_2$)=395.44, (M+H)$^+$=396

EXAMPLE 204

2-({5-Fluoro-2-[(4-formylphenyl)amino]-4-pyrimidinyl}amino)-N-(1-methylethyl)benzamide

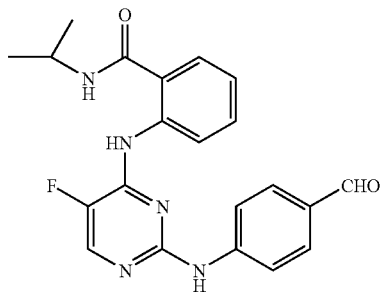

A 50-mL of round bottom flask was charged with 2-[(5-fluoro-2-{[4-(hydroxymethyl)phenyl]amino}-4-pyrimidinyl)amino]-N-(1-methylethyl)benzamide (200 mg, 0.5 mmol, 1.0 eq) and dioxane (20 mL). MnO$_2$ (217 mg, 2.5 mmol, 5.0 eq) was added slowly to this solution. Upon completion of the addition, the reaction mixture was heated at reflux for 16 h. The reaction mixture was filtered through celite and the solvent was evaporated to produce the desired product (189 mg, 48% yield) which was found to be 82% pure by HPLC. MS: M($C_{21}H_{20}FN_5O_2$)=393.42, (M+H)$^+$=394. This crude material was used for next step without further purification.

EXAMPLE 205

2-[(5-Fluoro-2-{[4-({[2(methylsulfonyl)ethyl]amino}methyl)phenyl]amino}-4-pyrimidinyl)amino]-N-(1-methylethyl)benzamide

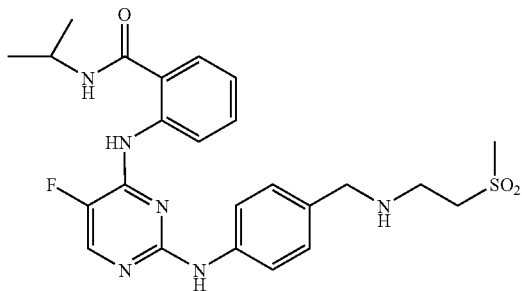

2-({5-Fluoro-2-[(4-formylphenyl)amino]-4-pyrimidinyl}amino)-N-(1-methylethyl)benzamide (80 mg, 0.2 mmol, 1.0 eq), [2-(methylsulfonyl)ethyl]amine (100 mg, 0.6 mmol, 3.0 eq), and CH$_2$Cl$_2$ (2.0 mL) were added to a vessel, which was sealed and stirred at room temperature for 16 h. Solvent was removed by evaporation to leave a residue. NaBCNH$_4$ (37 mg, 0.6 mmol, 3.0 eq) in CH$_2$Cl$_2$ (2.0 mL) was added was added to the residue and the reaction mixture was stirred at room temperature until the reaction was substantially complete, as determined by HPLC. The final product was purified by preparative HPLC using water (0.1% formic acid); acetonitrile (0.1% formic acid) as mobile phase. The desired compound was isolated as an off-white solid. (20 mg, 20% yield) MS: M($C_{24}H_{29}FN_6O_3S$)=500.60, (M+H)$^+$=501.

EXAMPLES 206-210

The following examples were prepared using a procedure substantially as described for the preparation of Example 205.

| Ex. No. | R | Mass (M + H)$^+$ |
|---|---|---|
| 206 | ˙˙˙⁀⁀OH | 439 |
| 207 | ˙˙˙⁀⁀S(=O)$_2$CH$_3$ | 501 |
| 208 | ˙˙˙⁀S(=O)$_2$⁀OH | 531 |
| 209 | ˙˙˙⁀⁀OCH$_3$ | 453 |

INTERMEDIATE 152

(5R)-5-Methyl-1-(3-nitrophenyl)-4-(trifluoroacetyl)-2-piperazinone

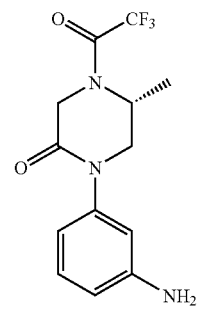

3-Nitroaniline (5.0 g, 36.2 mmol) was combined with EtOAc (50 mL) and 20% aq potassium bicarbonate (25 mL). The biphasic mixture was cooled to 0° C. (ice water bath) and treated with chloroacetyl chloride (2.9 mL, 36.2 mmol) dropwise over 30 min. The reaction mixture was warmed up to room temperature and stirred for 30 min. The reaction mixture was followed up by HPLC. The aqueous layer was removed. The organic layer was combined with (2R)-2-amino-1-propanol (8.5 mL, 108.6 mmol), heated to 60° C. for 3 h. HPLC analysis showed no SM was left. Water was added to reaction mixture and reheated to 60° C. The aqueous layer was removed and organic layer was washed by brine (60 mL×3). Evaporated solvent to dryness on vacuum and the yellow solid was stirred with 100 mL of 30% EtOAc in hexane. The solid was collected and washed with solvent (30% EtOAc in Hexane) 70 mL×3. The off white solid was collected and examined by HPLC and ¹H NMR. The solid was dried on high vacuum over night which produced a off white solid N²-[(1R)-2-hydroxy-1-methylethyl]-N¹-(3-nitrophenyl)glycinamide (5.65 g, 62% yield). MS: $M(C_{11}H_{15}N_3O_4)=253.26$ $(M+H)^+=254$.

To a solution of N²-[(1R)-2-hydroxy-1-methylethyl]-N¹-(3-nitrophenyl)glycinamide (2.0 g, 7.9 mmol) and tributylphosphine (2.7 mL, 15.8 mmol) in EtOAc (21 mL) was slowly added a solution of di-t-butylazodicarboxlate, (3.6 g, 15.8 mmol) in EtOAc 10 mL. The inside temperature was kept between 25° C. to 30° C. The reaction was followed by HPLC. The crude material was purified a silica gel column chromatography (2% to 5% MeOH in CH₂Cl₂). The compound (5R)-5-methyl-1-(3-nitrophenyl)-2-piperazinone was isolated as solid (690 mg, 37% yield) MS: $M(C_{11}H_{13}N_3O_3)=235.24$ $(M+H)^+=236$.

To a solution of (5R)-5-methyl-1-(3-nitrophenyl)-2-piperazinone (640 mg, 2.72 mmol) and Hunig base (0.56 mL, 3.26 mmol) in CH₂Cl₂; trifluoroacetic anhydride was added at 0° C. Then reaction mixture was warmed up to room temperature for 1 h. Reaction mixture was participated between water and CH₂Cl₂. The organic phase was then washed by brine and dried over MgSO4. The solvent was evaporated to dryness which gave the title product was used for next step without further purification. MS: $M(C_{11}H_{13}N_3O)_3)=235.24$ $(M+H)^+=236$.

Compound (5R)-5-methyl-1-(3-nitrophenyl)-4-(trifluoroacetyl)-2-piperazinone (860 mg, 2.6 mmol) was dissolved in 20 mL methanol with 8 mg (10% weigh of SM) of 10% Pd/C. The reaction mixture was degassed by nitrogen then was H₂ balloon over night. The reaction was followed by HPLC. The Pd/C was removed by filtration on celite. And the solvent was evaporated on high vacuum which gave the title product (692 mg, 88% yield) MS: $M(C_{13}H_{12}F_3N_3O_4)=331.25$, $(M+H)^+=332$.

EXAMPLE 210

2-{[5-fluoro-2-({3-[(5R)-5-methyl-2-oxo-1-piperazinyl]phenyl}amino)-4-pyrimidinyl]amino}-N-(1-methylethyl)benzamide

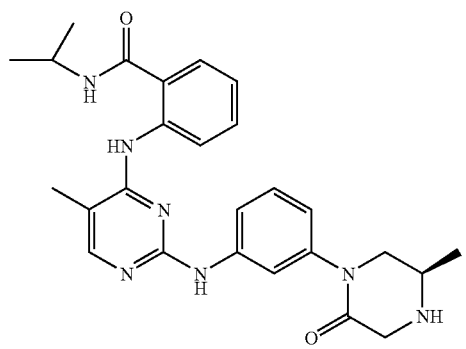

To the suspension solution of 2-[(2-chloro-5-fluoro-4-pyrimidinyl)amino]-N-(1-methylethyl)benzamide (100 mg, 0.32 mmol) and (5R)-1-(3-aminophenyl)-5-methyl-4-(trifluoroacetyl)-2-piperazinone (147 mg, 0.48 mmol) was added 2 drops of 12N HCl. The reaction mixture was then sealed and heated in a 95° C. oil bath for 16 h. The reaction was followed by LC/MS. The reaction was evaporated to dryness. The residue was then dissolved in THF (10 mL) with LiOH (1.0 M solution 0.64 mL). The reaction mixture was heated at 50° C. for 3 h. Then the solvent was evaporated to dryness on high vacuum and the residue was loaded on silica gel column and eluted with 2.0 to 9.0% MeOH (with 0.1% NH₄OH) in CH₂Cl₂. Oil was then recrystalized from hot EtOH to yield the pure title compound (84 mg, 55%). MS: $M(C_{25}H_{28}FN_7O_2)=477.54$ $(M+H)^+=478$.

EXAMPLES 211-212

The following examples were prepared by a process substantially as described for the preparation of Example 210.

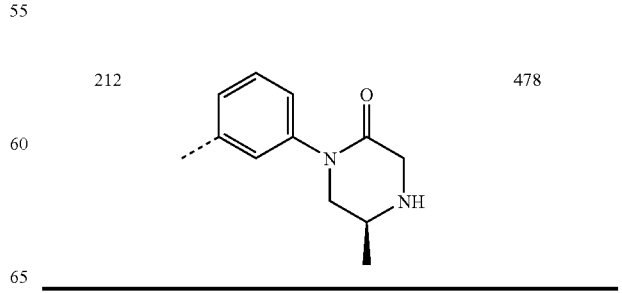

The invention claimed is:

1. A compound or a pharmaceutically acceptable salt thereof, which compound is N-(1-methylethyl)-2-[(5-methyl-2-{[3-(4-methyl-2-oxo-1-piperazinyl)phenyl]amino}-4-pyrimidinyl)amino]benzamide.

2. The compound of claim 1.

3. The pharmaceutically acceptable salt of the compound of claim 1.

4. A composition comprising a) the compound of claim 1 or a pharmaceutically acceptable salt thereof; and b) at least one pharmaceutically acceptable excipient.

* * * * *

```
                            SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: fluorescein-labeled synthetic peptide

<400> SEQUENCE: 1

Gly Arg Thr Gly Arg Arg Asn Ser Ile
 1               5
```